(12) United States Patent
Norman et al.

(10) Patent No.: US 8,263,795 B2
(45) Date of Patent: Sep. 11, 2012

(54) COPPER PRECURSORS FOR THIN FILM DEPOSITION

(75) Inventors: John Anthony Thomas Norman, Encinitas, CA (US); Melanie K. Perez, Escondido, CA (US)

(73) Assignee: Air Products and Chemicals, Inc., Allentown, PA (US)

(*) Notice: Subject to any disclaimer, the term of this patent is extended or adjusted under 35 U.S.C. 154(b) by 854 days.

(21) Appl. No.: 12/258,996

(22) Filed: Oct. 27, 2008

(65) Prior Publication Data

US 2009/0114874 A1    May 7, 2009

Related U.S. Application Data

(60) Provisional application No. 60/985,428, filed on Nov. 5, 2007.

(51) Int. Cl.
*C07F 7/10* (2006.01)
*C07F 1/08* (2006.01)
*C23C 16/00* (2006.01)
*H01L 29/12* (2006.01)

(52) U.S. Cl. ............... 556/12; 252/62.3 E; 427/255.28

(58) Field of Classification Search .............. 556/12; 252/62.3 E; 427/255.28
See application file for complete search history.

(56) References Cited

U.S. PATENT DOCUMENTS

| | | | |
|---|---|---|---|
| 5,098,516 A | 3/1992 | Norman et al. | |
| 6,538,147 B1 | 3/2003 | Choi | |
| 6,552,209 B1 | 4/2003 | Lei et al. | |
| 6,818,783 B2 | 11/2004 | Norman et al. | |
| 6,869,876 B2 | 3/2005 | Norman et al. | |
| 7,034,169 B1 | 4/2006 | Norman | |
| 7,205,422 B2 * | 4/2007 | Norman | 556/32 |
| 2003/0129308 A1 | 7/2003 | Chen et al. | |
| 2004/0247905 A1 | 12/2004 | Bradley et al. | |

FOREIGN PATENT DOCUMENTS

| | | |
|---|---|---|
| EP | 2 014 790 A1 | 1/2009 |
| JP | 06145986 | 11/1992 |
| WO | WO 0166347 A1 | 3/2000 |
| WO | WO 0168580 A1 | 3/2000 |
| WO | 2008/085426 A1 | 7/2008 |

OTHER PUBLICATIONS

Soininen, P.J., et al; "Reduction of Copper Oxide Film to Elemental Copper"; Journal of the Electrochemical Society; vol. 152 (2); pp. G122-G125; 2005.
Martensson, et al., "Atomic Layer Epitaxy of Copper", J. Electrochem. Soc., vol. 145, No. 8, Aug. 1998, pp. 2926-2931.
Awaya, et al., "Double-Level Copper Interconnections Using Selective Cooper CVD", Journal of Electronic Materials, vol. 21, No. 10, 1992, pp. 959-964.
Fine, et al., "Organometallic Chemical Vapor Deposition of Copper From a New Organometallic Precursor", Mat. Res. Soc. Symp. Proc., vol. 204, 1991, pp. 415-420.
Beach, et al., "Low-Temperature Chemical Vapor Deposition of High-Purity Copper from an Organometallic Source", Chem. Mater. 1990, 2, 216-219.

(Continued)

*Primary Examiner* — Porfirio Nazario Gonzalez
(74) *Attorney, Agent, or Firm* — Rosaleen P. Morris-Oskanian

(57) ABSTRACT

Non-fluorinated copper precursors and methods for making and using same are described herein. In certain embodiments, the copper precursors described herein may be used as precursors to deposit copper films and alloys thereof on a substrate through, for example, atomic layer deposition or chemical vapor deposition conditions.

14 Claims, 9 Drawing Sheets

OTHER PUBLICATIONS

Kroger, et al., "Properties of Copper Films Prepared by Chemical Vapor Deposition for Advanced Metallization of Microelectronic Devices", Journal of the Electrochemical Society, 146 (9) 3248-3254 (1999).

Shin, et al., "Synthesis of Volatile, Fluorinated B-Ketoiminato Copper(i) Complexes", J. Chem. Soc., Chem. Commun., 1992, pp. 217-219.

CA Selects: Chemical Vapor Deposition (CVD), Issue 7, 1996, p. 16.

* cited by examiner

SIMS profile of a CVD-deposited copper film on TiN from Example 2

EDX of copper film on ruthenium barrier from Example 4

COPPER PRECURSORS FOR THIN FILM DEPOSITION

CROSS-REFERENCE TO RELATED APPLICATIONS

This application claims the benefit of U.S. Provisional Application No. 60/985,428, filed Nov. 5, 2007. The disclosure of this provisional application is incorporated herein by reference in its entirety.

BACKGROUND OF THE INVENTION

The present invention generally relates to copper precursors that are used to deposit thin copper films. More specifically, the present invention relates to non-fluorinated copper precursors which are volatile, thermally stable and can be used, for example, to deposit thin copper films using atomic layer deposition (ALD) or chemical vapor deposition (CVD) processes.

The semiconductor industry uses metal-containing interconnects, such as copper (Cu), in electronic devices such as, for example, state of the art microprocessors. The metal-containing interconnects, which may be embedded fine metal lines, form the three dimensional grid upon which millions of transistors at the heart of the microprocessor can communicate and perform complex calculations. In these and other applications, copper or alloys thereof may be chosen over other metals such as, for example, aluminum because copper is a superior electrical conductor, thereby providing higher speed interconnections of greater current carrying capability.

Interconnect (IC) pathways within electronic devices are typically prepared by the damascene process, whereby photolithographically patterned and etched trenches and vias in the dielectric insulator are coated with a conformal thin layer of a diffusion barrier material. A diffusion barrier layer is typically used in conjunction with a metal or copper layer to prevent detrimental effects caused by the interaction or diffusion of the metal or copper layer with other portions of the integrated circuit. Exemplary barrier materials include, but are not limited to, titanium, tantalum, tungsten, chromium, molybdenum, zirconium, ruthenium, vanadium, palladium and/or platinum as well as carbides, nitrides, carbonitrides, silicon carbides, silicon nitrides, and silicon carbonitrides of these materials and alloys comprising same. In certain processes, such as when, for example, the interconnect comprises copper, the diffusion barrier layer may be coated with a thin 'seed' or 'strike' layer of copper, prior to completely filling in the features with pure copper. In still other cases, the seed layer of copper may be replaced by—or used in addition to—an analogous cobalt or similar conducting thin film 'glue' layer. Excess copper may then removed by the process of chemical mechanical polishing. Since the smallest features to be filled can be less than 0.2 microns wide and over 1 micron deep, it is preferable that the copper seed layer, copper glue layer and/or the diffusion barrier layers be deposited using metallization techniques that are capable of evenly filling these features, without leaving any voids, which could lead to electrical failures in the finished product.

In addition to the aforementioned processes for building the interconnect pathways within silicon chips, there is also the new and rapidly emerging technology of three-dimensional (3D) packaging which requires the fabrication of relatively larger scale copper interconnects known as TSV (Through Silicon Vias). TSV refers to the relatively large conducting vias which, when run through thinned IC, memory, or Micro Electromechanical (MEMS) silicon chips, enable them to be stacked and wired together into high functioning energy efficient devices that bear a small footprint. There are a number of approaches to 3-D packaging. The 'via first' approach entails first etching vias into the silicon wafer, filling them with copper before doing the Complementary Metal Oxide Semiconductor (CMOS) or before doing Back End of Line (BEOL) processing on top of the wafer. The wafer underside is then thinned and multiple chips from it are stacked and bonded. The 'via last' approach has two methods. The first method involves etching and filling the vias after BEOL, then sequentially thinning, stacking, and bonding the devices together. The second method involves taking finished wafers, thinning them, stacking them and bonding them, then etching vias through the stack and filling the vias with copper. Each approach to 3-D packaging has its own pros and cons. For instance, in the 'via last' approach, there can still be some signal routing possible above the TSVs whereas via first permits the TSV vias to be constructed in unthinned (i.e., mechanically robust) wafers. In all cases, TSV vias are relatively deep because they need to span the entire thickness of the thinned silicon wafer, which is oftentimes greater than 100 microns deep. The density of these interconnects can be in the region of $10^4$ vias/mm$^2$ of silicon surface. Once the chips are stacked and aligned, the vias are fused together by a variety of techniques to form continuous conducing lines thereby 'wiring' the chips together.

There are many reasons behind the growing importance and pursuit of TSV. The device density and short conducting pathways between chips that it affords directly translates to compact, high performance low energy consuming systems that are critical for the burgeoning mobile application markets such as, for example, camera phones, i-phones, personal data assistant (PDA) devices, global positioning systems (GPS), and the like where miniaturization and battery life are of paramount importance. Another very important factor driving TSV 3-D packaging is that since the TSV vias represent a 3 orders of magnitude shortening of the typical interchip interconnects encountered using other packing techniques such as Package on a Package (PoP), System in a Package (SiP) and System on a Chip (SoC), the clock speed of the resulting packages can rival or equal that of devices manufactured at finer geometries. TSV therefore presents a strong economic driver by not needing to stay on the CMOS shrink curve. For instance, an IC with stacked memory shows a 1000 fold increase in speed with a 100 fold decrease in power consumption by eliminating the signal delays and power consumption from horizontal wiring.

Numerous methods such as ionized metal plasma (IMP), physical vapor deposition (PVD), chemical vapor deposition (CVD), atomic layer deposition (ALD), cyclic chemical vapor deposition (CCVD), plasma-assisted chemical vapor deposition (PACVD), plasma-enhanced chemical vapor deposition (PECVD), electroplating, and electroless plating have been used to deposit metal-containing layers such as the metallization, diffusion barrier, and/or other layers. Among them, CVD and ALD methods using one or more organometallic precursors may be the most promising methods because these methods provide excellent step coverage for high aspect ratio structures and good via filling characteristics. In a typical CVD process, a vapor of a volatile organometallic precursor containing the desired metal is introduced to a substrate surface whereupon a chemical reaction occurs in which a thin film containing the metal as a compound or as a pure element is deposited on the substrate. Since the metal is typically delivered in a vapor form as a volatile precursor, it can access both vertical and horizontal surfaces to provide an evenly distributed thin film. In a typical ALD process, a volatile organometallic precursor is alternately pulsed into a reactor with a reagent gas such that self-limiting alternating monolayers of precursor/reagent are deposited on the substrate wherein the monolayers react together to form a metal film or a metal-containing film which is subsequently reduced to metal or used as deposited. For example, if a copper organometallic precursor was reacted with a suitable oxidant in an ALD process, the resulting cuprous oxide or cupric oxide monolayer or multilayer could be used for semiconductor applications or reduced to copper metal.

For copper thin films, some of the same precursors suitable for CVD and other depositions may also be suitable as ALD precursors. In certain applications, it may be preferable that the precursor be highly volatile, deposit copper films that are substantially pure (i.e., have a purity of about 95% or about 99% or greater copper), and/or minimize the introduction of potentially contaminating species into the reaction chamber or onto the diffusion barrier or other underlying surfaces. Further, in these applications, it may be preferable that the copper film exhibits good adhesion to the diffusion barrier layer because poor adhesion may lead to, inter alia, delamination of the copper film during chemical mechanical polishing.

Several organometallic precursors have been developed to deposit low electrical resistivity copper films by the aforementioned processes, particularly CVD or ALD processes. Two of often-used families of copper organometallic precursors that have been studied extensively are the Cu(I) and Cu(II) precursors. One commonly used Cu(i) precursor is a precursor having the formula "Cu(I)(hfac)(W)" precursor where "hfac" represents the 1,1,1,5,5,5-hexafluoro-2,4-pentanedionate anion and (W) represents a neutral stabilizing ligand, such as, for example, an olefin, an alkyne, or a trialkylphosphine. One particular example of a Cu(I) precursor having the above formula is 1,1,1,5,5,5-hexafluoro-2,4-pentanedionato-copper (I) trimethylvinylsilane (hereinafter Cu(hfac)(tmvs)), which is sold under the trademark CUPRASELECT™ by Air Products and Chemicals, Inc. of Allentown, Pa., the assignee of the present application. These Cu(I) precursors can deposit films via a disproportionation reaction whereby two molecules of the precursor react on a heated substrate surface to provide copper metal, two molecules of free ligand (W), and the volatile by-product $Cu^{(+2)}(hfac)_2$. Equation (1) provides an example of a disproportionation reaction:

$$2Cu^{(+1)}(hfac)W \rightarrow Cu+Cu^{(+2)}(hfac)_2+2W \quad (1)$$

In CVD depositions, the disproportionation reaction illustrated in Equation (1) is typically run at a temperature of around 200° C.; however, other temperatures may be used depending upon the deposition process. As Equation (1) illustrates, the $Cu^{(+2)}(hfac)_2$ constitutes a byproduct from the reaction and may need to be removed from the reaction chamber.

Yet another type of Cu(I) precursor is a precursor having the formula "(Y)Cu(Z)". In these particular Cu(I) precursors, "Y" is an organic anion and "Z" is a neutral stabilizing ligand, such as, for example, trialkylphosphine. An example of such a precursor is $CpCuPEt_3$, where Cp is cyclopentadienyl and $PEt_3$ is triethylphoshine. Under typical CVD conditions, two of these precursor molecules may react on a wafer surface, whereby the two stabilizing trialkyphosphine Z ligands become disassociated from the copper centers, the two (Y) ligands become coupled together, and the copper (I) centers are reduced to copper metal. The overall reaction is shown below in Equation (2).

$$2(Y)Cu(Z) \rightarrow 2Cu+(Y-Y)+2(Z) \quad (2)$$

However, in certain instances, this type of chemistry may present problems because the released trialkylphosphine ligands may contaminate the reaction chamber and act as undesired N-type silicon dopants.

As mentioned previously, yet another type of precursor used to deposit copper-containing films is Cu(II) precursors. Unlike the Cu(I) precursors, the Cu(II) precursors require the use of an external reducing agent such as, for example, hydrogen or alcohol to deposit copper films that are largely free of impurities. An example of a typical Cu(II) precursor has the chemical formula $Cu(II)(Y)_2$ wherein (Y) is an organic anion. Examples of this type of precursor include, but are not limited to, Cu(II)bis(β-diketonates), Cu(II) bis(β-diimine), and Cu(II) bis(β-ketoimine) compounds. Equation (3) provides an illustration of a deposition reaction wherein hydrogen is used as the reducing agent.

$$Cu(II)(Y)_2+H_2 \rightarrow Cu+2YH \quad (3)$$

The Cu(II) precursors are typically solids and the temperatures required for film deposition are typically above 200° C.

In addition to the copper precursors described above, U.S. Pat. No. 7,205,422, which is commonly assigned to the assignee of the present application and incorporated herein by reference, describes non-fluorinated as well as fluorinated metal precursors which are suitable for ALD or CVD depositions of thin metal films.

In certain applications such as 3-D packaging, it is desirable to provide a copper metallization process which is cost effective and rapid. To use copper electroplating to fill these features, a seed layer of copper is first needed to line the inside of the TSV features. Currently, physical vapor deposition (PVD) copper is used for this purpose, but this line-of-sight technique is typically limited in its ability to provide vertical sidewall coverage. This is particularly problematic for TSV vias due to its relatively great depth. In addition, as 3-D packaging evolves, the density of TVS per unit area will increase and thereby drive the ratio of via depth to diameter higher to minimize the surface area of the chip that is consumed. This increased aspect ratio will further compromise the ability of PVD to provide adequately conformal copper seed layers with good sidewall coverage. For these reasons, CVD copper represents an excellent technology for proving good sidewall coverage and possibly a means by which to fill entire TSV structures with copper in one step. Thus, good CVD copper precursor may need to be thermally stable yet chemically reactive to permit high vapor pressures of precursor and high growth rates of copper respectively.

Accordingly, there is a need in the art for copper precursors that exhibit at least one of the following properties in ALD or CVD processing: thermal stability, chemically reactive, volatility, and allows for a high growth rate of copper metal.

BRIEF SUMMARY OF THE INVENTION

Volatile copper precursors, particularly non-fluorinated copper precursors, and methods for making and using same, such as for example as a precursor in a deposition process, are described herein. In one aspect, there is provided a copper precursor represented by formula (I):

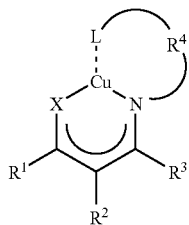

(I)

wherein X is selected from oxygen and $NR^5$;

wherein $R^1$, $R^2$, $R^3$, and $R^5$ are each independently selected from a hydrogen atom; a halogen atom; a nitro group having a formula $NO_2$; an alkyl having a formula $C_nH_{2n+1}$ wherein n is a number ranging from 1 to 20; an alkylsilane having a formula $(R^6)_3Si$ wherein $R^6$ is each independently an alkyl, an alkoxy or an amide comprising from 1 to 20 carbon atoms; an aryl group comprising from 6 to 12 carbon atoms; an alkyl-substituted aryl comprising from 6 to 12 carbon atoms; an ether having a formula $(CH_2)_nO(C_mH_{2m+1})$ where n and m are independently a number ranging from 1 to 20; a silylether having a formula $(R^7)_3SiO$ wherein $R^7$ is each independently an alkyl comprising from 1 to 20 carbon atoms or an aryl comprising from 6 to 12 carbon atoms; an alkoxy comprising from 1 to 20 carbon atoms; and an amide comprising from 1 to 20 carbon atoms;

wherein $R^4$ is selected from an alkyl having a formula $C_nH_{2n+1}$ wherein n is a number ranging from 1 to 20; an alkylsilane having a formula $(R^6)_3Si$ wherein $R^6$ is each independently an alkyl, an alkoxy or an amide comprising from 1 to 20 carbon atoms; an aryl comprising from 6 to 12 carbon atoms; an alkyl-substituted aryl comprising from 6 to 12 carbon atoms; a silylether having a formula $(R^7)_3SiO$ wherein $R^7$ is each independently an alkyl group comprising from 1 to 20 carbon atoms or an aryl group comprising from 6 to 12 carbon atoms; an alkoxy comprising from 1 to 20 carbon atoms; and an amide comprising from 1 to 20 carbon atoms and wherein $R^4$ associates with L by having a hydrogen, an atom, or a group removed;

wherein L is a ligand selected from an alkylnitrile comprising from 2 to 20 carbon atoms; a silylnitrile having the formula $(R^8)_3SiCN$ wherein $R^8$ is each independently an alkyl, an alkoxy, or an amide comprising from 1 to 20 carbon atoms; an alkyne comprising from 1 to 20 carbon atoms; a silylalkyne having a formula $(R^9)_3SiCCR^{10}$ wherein $R^9$ is each independently an alkyl, an amide, or an alkoxy comprising from 1 to 20 carbon atoms and $R^{10}$ is hydrogen, an alkoxy, an amide, or an alkyl comprising from 1 to 20 carbon atoms; a silylalkyne having a formula $(R^{11})_3SiCCSi(R^{11})_3$ wherein $R^{11}$ is each independently an alkyl, an amide, or an alkoxy comprising from 1 to 20 carbon atoms; an alkene, diene, or triene comprising from 1 to 20 carbon atoms; a silylalkene having a formula $(R^{12})_3SiCR^{13}C(R^{13})_2$ wherein $R^{12}$ is each independently an alkyl, an alkoxy, an aryl, a vinyl, or an amide comprising from 1 to 20 carbon atoms and $R^{13}$ is each independently a hydrogen, an alkyl comprising from 1 to 20 carbon atoms, or an aryl comprising from 6 to 12 carbon atoms; a bis(silyl)alkene having the formula $(R^{14})_3SiCR^{13}CR^{13}Si(R^{14})_3$ wherein $R^{14}$ is each independently an alkyl, an alkoxy, or an amide comprising from 1 to 20 carbon atoms and $R^{13}$ is each independently a hydrogen atom or an alkyl comprising from 1 to 20 carbon atoms; an allene comprising from 3 to 20 carbons; an allene having a formula $(R^{15})_2CCC(R^{15})_2$ where $R^{15}$ is each independently a hydrogen atom or an alkyl silane having a formula $(R^{16})_3Si$ wherein $R^{16}$ is each independently an alkyl, an amide, or an alkoxy comprising from 1 to 20 carbon atoms; an alkylisocyanide having a formula $R^{17}NC$ wherein $R^{17}$ is an alkyl comprising from 1 to 20 carbon atoms; a silylisocyanide having a formula $(R^{18})_3SiNC$ wherein $R^{18}$ is each independently an alkyl comprising from 1 to 20 carbon atoms; and an aryl group comprising from 6 to 12 carbon atoms and wherein L associates with $R^4$ by having a hydrogen, an atom, or a group removed; and wherein an organometallic bond between M and L is selected from two single bonds or one single bond.

In one embodiment, the precursor comprises a compound having the above formula (I) wherein $R^1$ and $R^3$ are both the alkyl group methyl; $R^2$ is a hydrogen atom; X is an oxygen atom; the ligand L comprises the silylalkene having a formula $(R^{12})_3SiCR^{13}C(R^{13})_2$ wherein $R^{12}$ comprises the vinyl group and $R^{13}$ comprises the Me group and $R^4$ comprises the alkoxy group wherein L and $R^4$ associate with each other having a Me group removed from L and H removed from $R^4$. In this or other embodiments, $R^4$ is the alkoxy group $OCH_2CH_2$. In a further embodiment, $R^4$ is the alkyoxy group $OCHMeCH_2$.

In another aspect, there is provided a process for depositing a film comprising copper on a substrate comprising: contacting the substrate with a copper precursor having the above formula (I) wherein the contacting is conducted under conditions sufficient for the precursor to react and form the film.

In a further aspect, there is provided an electronic device comprising a film comprising copper wherein the film is deposited via a method selected from chemical vapor deposition and atomic layer deposition using a copper precursor having the above formula (I) and a reducing agent comprising formic acid.

In yet another aspect, there is provided a method of making a copper precursor having the above formula (I) where X is oxygen comprising: preparing a primary amine having a formula $H_2NR^4L$ wherein $R^4$ and L are as described above; condensing the primary amine with a β-diketone having a formula $R^1C(O)CHR^2C(O)R^3$ to form an intermediate β-ketoimine product having a formula $R^1C(O)CHR^2C(NR^4L)R^3$ wherein $R^1$, $R^2$, $R^3$, $R^4$, and L are as described above and deprotonating the β-ketoimine intermediate product using a base in the presence of a metal source to form the copper precursor.

In a further aspect, there is provided a method of making a copper precursor having the above formula (I) wherein X is oxygen comprising: condensing an amine having a formula $H_2NR^4$ with a β-diketone having a formula $R^1C(O)CHR^2C(O)R^3$ to form a first intermediate β-ketoimine product having a formula $R^1C(O)CHR^2C(NR^4)R^3$ wherein $R^1$, $R^2$, $R^3$, and $R^4$ are as described above; attaching a ligand (L) to $R^4$ in the first intermediate β-ketoimine product to provide a second intermediate β-ketoimine product having a formula $R^1C(O)CHR^2C(NR^4L)R^3$ wherein $R^1$, $R^2$, $R^3$, $R^4$, and L are as described above; deprotonating the second β-ketoimine intermediate product using a base in the presence of a metal source to form the copper precursor.

BRIEF DESCRIPTION OF SEVERAL VIEWS OF THE DRAWINGS

FIG. 1 also provides the differential scanning calorimetry (DSC) for this precursor as shown by the dotted line.

FIG. 2 also provides the differential scanning calorimetry (DSC) for the precursor as shown by the dotted line.

DETAILED DESCRIPTION OF THE INVENTION

Figure 1:
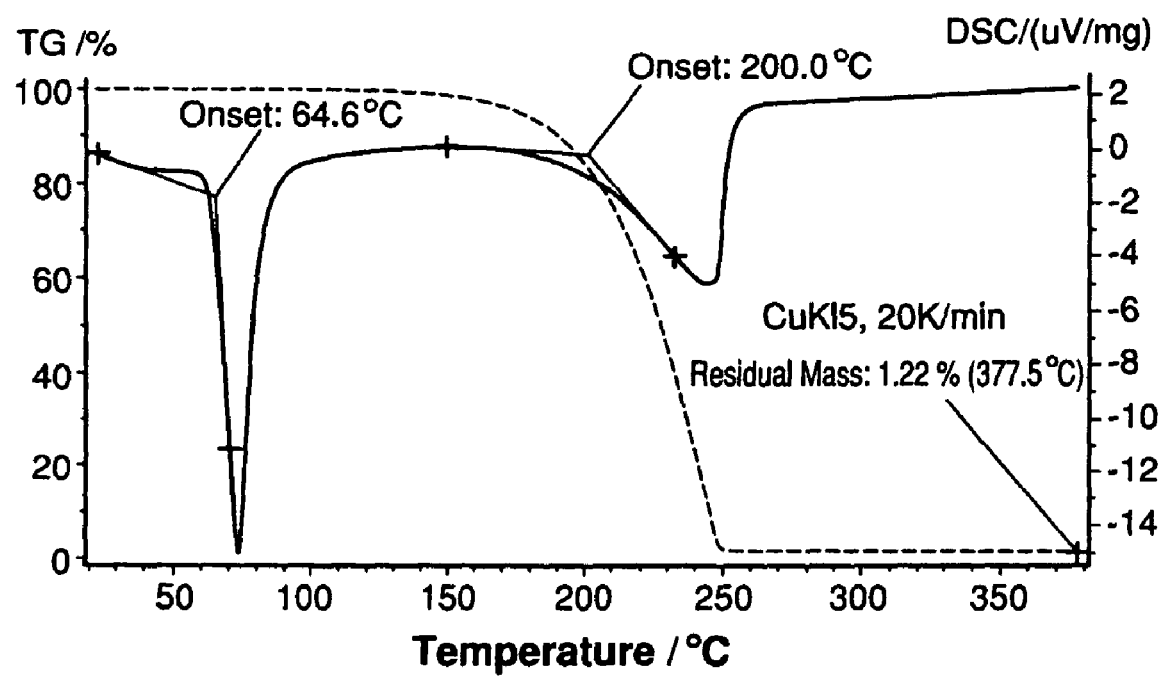
FIG. 1 provides the thermogravometric analysis (TGA) of the evaporation of the precursor copper(N(2(vinyldimethylsiloxy)propyl)-2-imino-4-pentenoate) or Cu(MeC(O)CHC(NCH$_2$CHMeOSiMe$_2$C$_2$H$_3$)Me) wherein "Me" as used herein stands for a methyl group.

Copper precursors, particularly copper (I) complexes, and methods for making and using same are described herein. The copper precursors may be used, for example, as precursors to deposit metal films or metal-containing films via a variety of deposition processes, including CVD or ALD processes.

The copper precursors described herein provide one or more advantageous properties due to their unique structure. The combination of relatively high thermal stability, relatively high chemical reactivity, and relatively high volatility that the copper precursors described herein exhibit—compared to other organometallic metal precursors in the art—may be desirable for CVD and ALD processes. For CVD systems, it is desirable that the reaction of the precursor occur only on the heated substrate surface rather than during vapor delivery and/or in the processing chamber. For ALD systems, it is desirable that the metal precursor react at specific sites while not suffering unwanted thermal degradation during vapor delivery and/or in the processing chamber.

The non-fluorinated copper precursors described herein posses an unexpected and highly desirable combination of chemical and physical properties. These properties include being thermally stable at relatively high temperatures to permit the release and delivery of a high vapor pressure of stable precursor vapor into the ALD or CVD reactor. For example, for one embodiment of the precursor described herein or copper(N(2(vinyldimethylsiloxy)propyl)-2-imino-4-pentenoate), the precursor exhibited constant evaporation at temperatures of up to 250° C., as established by TGA, at a heating ramp of 10° C./minute under a flowing nitrogen atmosphere at one atmosphere pressure. In additional experiments for the same precursor, it was shown that holding samples at 170° C. and 150° C. resulted in complete evaporation after 50 and 160 minutes, respectively. Once inside the reactor, the vapor is contacted with a suitable reducing agent which chemically reacts with the precursor vapor at low temperatures (e.g., temperatures ranging from 50-400° C.) to deposit a copper film or alloy thereof. In certain embodiments, low temperature processing (e.g., 125° C. or less) may be particularly favorable for depositing, for example, continuous ultrathin copper seed layers onto diffusion barriers such as, but not limited to, ruthenium at high growth rates (e.g., about 50 Angstroms (Å)/minute or less or about 30 Å/minute or less) to help avoid the copper films from agglomerating into a discontinuous film. Since high vapor pressures of precursors described herein can be readily generated due to their thermal stability permitting high precursor temperatures to be used, a commensurately high growth rate of copper can be achieved. This may be desirable, for example, for those embodiments involving copper metallization of TSV features used in 3-D packaging where a high growth rate of copper is desired. In this or other embodiments, the high vapor pressure of the precursors described herein can also allow a high nucleation density of copper, especially at low deposition temperatures, to create exceptionally thin and continuous copper films.

As previously discussed, the precursors described herein are non-fluorinated. In certain embodiments, it is preferable to use non-fluorinated precursors over their fluorinated counterparts to avoid the potential release of this element during the copper deposition process which can then migrate into barrier and/or other layers and ultimately impact device performance. The challenge in creating such non-fluorinated precursor is that fluorinated precursors are generally much more stable and more volatile than their unfluorinated counterparts. These two properties are synergistic because as the molecule evaporates at a relatively low temperature, it does not experience high temperatures before it is all vaporized. By contrast, a non-fluorinated molecule typically is less volatile and less stable meaning that it needs to be heated more strongly to evaporate it into a vapor and at these elevated temperatures it starts to decompose. Thus, the vapor stream from the precursor tends to become polluted with volatile precursor decomposition products and a residue of involatile decomposition products accumulates in the precursor container. It is surprising and unexpected that the non-fluorinated precursors described herein are highly suited to ALD and CVD by being extremely stable and volatile, but also chemically reactive towards growing a copper film by CVD or ALD processes. The non-fluorinated copper precursors cleanly evaporate as they become heated and leave behind virtually no residue. Thus, the non-fluorinated precursors share the general advantages of fluorinated precursors yet are fluorine free.

The copper precursors described herein have a relatively high thermal stability which allows them to be delivered as a stable vapor into a CVD or ALD reactor. In this connection, it is believed that since ligand L is directly attached to the ketoimine or the diimine ligand, it is not able to readily disassociate from the metal center (M) as a free molecule, tending to keep ligand L coordinated to the metal center under conditions of low pressure and heat which would typically be sufficient to fully disassociate ligand L. This in contrast to analogous complexes where L is bonded only to the metal center. In alternative embodiments, subsistent group $R^4$, which associates the ketoimine or the diimine ligand with the ligand L, can be chemically engineered such that under the correct process conditions this association can be broken or disassociated to effectively release the ligand L. The term "associate" as used herein means to join the ketoimine or diimine ligand with ligand L and can include, but is not limited to, a chemical bond (e.g., covalent bond, hydrogen bond, etc.) an electrostatic attraction, Lewis acid-Lewis base interaction, and/or other means. In these embodiments and under certain processing conditions sufficient to release ligand L, it may allow, for example, the complex to disproportionate to give a metal film or a metal-containing film. Further, the disassociation of $R^4$ with ligand L may reduce the precursor into lower molecular weight units which are more readily desorbed during processing, for example, in a CVD or ALD reactor. For instance, if the precursor is fully reacted with water then the result of the disassociation would be copper oxide growth along with the release of hydrolyzed small molecular weight volatile ligand fragments. For example, copper precursor $Cu(Me(C(O)CHC(NCH_2CH_2NMeSiMe_2(C_2H_3))Me)$ (where the $C_2H_3$ group within the complex represents a vinyl group) reacts with water to yield solid cuprous oxide, $MeC(O)CH_2C(NCH_2CH_2NMeH)Me$, and $C_2H_3Me_2SiOH$, the latter of which couples to provide tetramethyldivinyldilsiloxane.

Another unique feature of these complexes is its ability to provide a metal center which is more sterically exposed on one face of the precursor. Typical β-ketoimine or β-diketone olefin compounds are flat molecules where the coordinating diketonate or ketoiminate anion, the metal center, and olefin all lie within the same plane. By contrast, the complexes described herein may allow for the complex's plane of coordination to become convexly bowed pushing the metal center more towards the underside of the complex thereby allowing it to be more exposed and accessible to surfaces and reagent molecules. For instance, in exemplary copper precursor $Cu(MeC(O)CHC(NCH_2CH_2OSiMe_2(C_2H_3))Me)$, the β-ketoiminate chelate ring is tilted approximately seven degrees away from the copper olefin coordination triangle thereby exposing the copper more on the underside of the molecule. This exposure and hence greater steric access may be important for certain ALD and CVD type processes because it can help the copper atom contained therein to adsorb onto the substrate surface. Further, by controlling the nature and the length of the $R^4$ association to ligand L, one can develop metal precursors that are relatively strained in their conformation to provide exposed metal centers. Releasing this strain by chemically breaking or disassociating the $R^4$ link with ligand L allows for relatively high reactivity. In other words, by adjusting the structure of these precursors, it should be possible to build complexes with internal strain that can be relieved by breaking the $R^4$ link to drive the molecule's decomposition into small volatile organic units while at the same time providing a sterically exposed metal center for high surface reactivity and metal deposition.

The copper precursors described herein are related to those described, for example, in U.S. Pat. Nos. 7,205,422 and 7,034,169 which are incorporated herein by reference in their entirety. In one embodiment, the copper precursors described herein have the following formula (I):

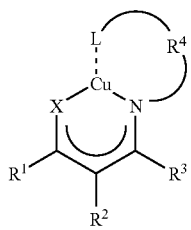

(I)

In formula (I), metal atom M is copper. In formula (I), X can be oxygen thereby forming a ketoiminate complex, or alternatively X can be $NR^5$ thereby forming a diiminate complex. In formula (I), substituents $R^1$, $R^2$, $R^3$, and $R^5$ are each independently selected from a hydrogen atom; a halogen atom; a nitro group having a formula $NO_2$; an alkyl having a formula $C_nH_{2n+1}$ wherein n is a number ranging from 1 to 20; an alkylsilane having a formula $(R^6)_3Si$ wherein $R^6$ is each independently an alkyl, an alkoxy or an amide comprising from 1 to 20 carbon atoms; an aryl group comprising from 6 to 12 carbon atoms; an alkyl-substituted aryl comprising from 6 to 12 carbon atoms; an ether having a formula $(CH_2)_nO(C_mH_{2m+1})$ where n and m are independently a number ranging from 1 to 20; a silylether having a formula $(R^7)_3SiO$ wherein $R^7$ is each independently an alkyl comprising from 1 to 20 carbon atoms or an aryl comprising from 6 to 12 carbon atoms; an alkoxy comprising from 1 to 20 carbon atoms; and an amide comprising from 1 to 20 carbon atoms. In formula (I), substituent $R^4$ is selected from an alkyl having a formula $C_nH_{2n+1}$ wherein n is a number ranging from 1 to 20; an alkylsilane having a formula $(R^6)_3Si$ wherein $R^6$ is each independently an alkyl, an alkoxy or an amide comprising from 1 to 20 carbon atoms; an aryl comprising from 6 to 12 carbon atoms; an alkyl-substituted aryl comprising from 6 to 12 carbon atoms; an ether having a formula $(CH_2)_nO(C_mH_{2m+1})$ where n and m are independently a number ranging from 1 to 20; a silylether having a formula $(R^7)_3SiO$ wherein $R^7$ is each independently an alkyl group comprising from 1 to 20 carbon atoms or an aryl comprising from 6 to 12 carbon atoms; an alkoxy comprising from 1 to 20 carbon atoms; and an amide comprising from 1 to 20 carbon atoms and wherein $R^4$ has a hydrogen, an atom, or a group removed to associate with L. Further, in formula (I), L is a ligand is a ligand selected from an alkylnitrile comprising from 2 to 20 carbon atoms; a silylnitrile having the formula $(R^8)_3SiCN$ wherein $R^8$ is each independently an alkyl, an alkoxy, or an amide comprising from 1 to 20 carbon atoms; an alkyne comprising from 1 to 20 carbon atoms; a silylalkyne having a formula $(R^9)_3SiCCR^{10}$ wherein $R^9$ is each independently an alkyl, an amide, or an alkoxy comprising from 1 to 20 carbon atoms and $R^{10}$ is hydrogen, an alkoxy, an amide, or an alkyl comprising from 1 to 20 carbon atoms; a silylalkyne having a formula $(R^{11})_3SiCCSi(R^{11})_3$ wherein $R^{11}$ is each independently an alkyl, an amide, or an alkoxy comprising from 1 to 20 carbon atoms; an alkene, diene, or triene comprising from 1 to 20 carbon atoms; a silylalkene having a formula $(R^{12})_3SiCR^{13}C(R^{13})_2$ wherein $R^{12}$ is each independently an alkyl, an alkoxy, vinyl, an aryl, or an amide comprising from 1 to 20 carbon atoms and $R^{13}$ is each independently a hydrogen or an alkyl comprising from 1 to 20 carbon atoms; a bis(silyl)alkene having the formula $(R^{14})_3SiCR^{13}CR^{13}Si(R^{14})_3$ wherein $R^{14}$ is each independently an alkyl, an alkoxy, or an amide comprising from 1 to 20 carbon atoms and $R^{13}$ is each independently a hydrogen atom or an alkyl comprising from 1 to 20 carbon atoms; an allene comprising from 3 to 20 carbons; an allene having a formula $(R^{15})_2CCC(R^{15})_2$ where $R^{15}$ is each independently a hydrogen atom, an alkyl silane having a formula $(R^{16})_3Si$ wherein $R^{16}$ is each independently an alkyl, an amide, or an alkoxy comprising from 1 to 20 carbon atoms; an alkylisocyanide having a formula $R^{17}NC$ wherein $R^{17}$ is an alkyl comprising from 1 to 20 carbon atoms; a silylisocyanide having a formula $(R^{18})_3SiNC$ wherein $R^{18}$ is each independently an alkyl, amide, or alkoxy comprising from 1 to 20 carbon atoms; and an aryl group comprising from 6 to 12 carbon atoms and wherein L has a hydrogen, an atom, or a group removed to associate with $R^4$.

The term "alkyl" as used herein includes straight chain, branched, or cyclic alkyl groups, comprising from 1 to 20 carbon atoms, or from 1 to 10 carbon atoms. Exemplary alkyl groups include methyl, ethyl, n-propyl, isopropyl, n-butyl, isobutyl, sec-butyl, tert-butyl, tert-amyl, n-pentyl, n-hexyl, cyclopentyl, and cyclohexyl. The term "alkyl" applies also to alkyl moieties contained in other groups such as haloalkyl, alkylaryl, or arylalkyl. The term "aryl" as used herein comprises 6 to 12 member carbon rings having aromatic character. Exemplary aryl groups include phenyl and napthyl groups. The term "alkyl-substituted aryl" applies to aryl moieties that are substituted with alkyl. Exemplary alkyl-substituted aryl groups include tolyl and xylyl groups. The term "halo" and "halogen" include fluorine, chlorine, bromine, or iodine. In certain embodiments, some of the groups discussed herein may be substituted with one or more other elements such as, for example, a halogen atom or other heteroatoms such as O, N, Si, or S.

In formula (I), substituent $R^4$ is selected such that it can associate with the ligand L. Further, ligand L is selected such that it can associate with $R^4$. It is believed that both ligand L and substituent $R^4$ have a hydrogen, atom, or group removed that allows $R^4$ and L to associate thereby connecting the ketoimine or diimine ligand of the complex with ligand L. In this connection, when L is silylalkene, one of its bonds is available to associate with $R^4$. One exemplary embodiment is shown in FIG. 1 or $Cu(MeC(O)CHC(NCH_2CH_2OSiMe_2(C_2H_3))Me)$. In this embodiment, X is oxygen, L has the formula $H_2C=CHSiMe_2$, $R^4$ is $OCH_2CH_2$, $R^3$ is hydrogen, and $R^1$ and $R^2$ are both methyl groups. In another embodiment where X is $NR^5$, $R^5$ and L can associate. In this embodiment, both ligand L and substituent $R^5$ have a hydrogen, atom, or group removed that allows $R^5$ and L to associate in the same fashion as $R^4$ and L are associated.

In certain embodiments, substituent $R^4$ may also be connected to substituents $R^1$, $R^2$ and/or $R^3$. In this embodiment, substituent $R^4$ can only connect with substituents $R^1$, $R^2$ and/or $R^3$ when $R^1$, $R^2$ and/or $R^3$ are neither a hydrogen atom, a halogen atom, nor the nitro group $NO_2$.

In certain embodiments, substituents $R^1$, $R^2$ and/or $R^3$ are each independently a hydrogen atom or an alkyl group. In one particular embodiment, substituents $R^1$ and $R^3$ can be the same or different alkyl groups and are each independently methyl, ethyl, propyl, isopropyl, butyl, sec-butyl, isobutyl, tert-butyl or combinations thereof. In this or other embodiments, X is an oxygen atom. In this or other embodiments, $R^2$ is a hydrogen atom. In this or other embodiments, ligand L comprises the silylalkene having a formula $(R^{12})_3SiCR^{13}C(R^{13})_2$ wherein $R^{12}$ comprises the vinyl group and $R^{13}$ comprises the alkyl group methyl or Me and $R^4$ comprises an alkoxy group comprising the formula wherein L and $R^4$ associate with each other by having a Me group removed from L and a H atom removed from $R^4$. In this or other embodiments, $R^4$ comprises an alkoxy having the formula $OCHMeCH_2$ or $OCH_2CH_2$.

In certain embodiments of the complex described herein, X is $NR^5$ and $R^5$ can be any of the groups or atoms described above for $R^1$, $R^2$, or $R^3$. In these embodiments, ligand (L), or alternatively an additional ligand (L) which can be any of the groups or atoms described above, can also be attached to substituent $R^5$ as well as substituent $R^4$. In these embodiments, it is believed that at least one ligand L has, for example, an available valence with which to associate with $R^5$ thereby connecting the diimine ligand of the complex with ligand L. In this or other embodiments, substituent $R^5$ can also be connected to any one or all of substituents $R^1$, $R^2$, $R^3$, and/or $R^4$ to form cyclic structures. In the latter embodiment, substituent $R^5$ connects with substituents $R^1$, $R^2$ and/or $R^3$ only when $R^1$, $R^2$ and/or $R^3$ are neither a hydrogen atom, a halogen atom, nor the nitro group $NO_2$, or alternatively when $R^5$ is a hydrogen atom.

In certain embodiments, substituent $R^4$, and/or optionally substituent $R^5$ if X is $NR^5$, may be adjusted such that the ligand L coordinates to the metal center of an adjacent complex rather than to its own metal center. In these embodiments, other complexes such as, but not limited to, dimeric, trimeric, and tetrameric complexes can form.

In certain embodiments, any one or all of substituents $R^1$, $R^2$, and $R^3$ can be independently connected to form cyclic structures. In certain embodiments, $R^1$ and $R^2$ and/or $R^2$ and $R^3$ can be independently connected to form cyclic structures.

In one embodiment, ligand L in formula (I) may be an alkylnitrile such as, but not limited to, $CH_2CN$ or $Me_2CH_2CCN$. In this and the foregoing embodiments for L, the groups defined for ligand L have a hydrogen removed to allow associating with $R^4$. In an alternative embodiment, ligand L in formula (I) may be a silyinitrile such as but not limited to $Me_2CH_2SiCN$. In a further embodiment, ligand L in formula (I) may be a alkyne such as but not limited to $CH_2CCMe$ or $CH_2CCH$. In another embodiment, ligand L in formula (I) may be a alkene such as but not limited to $Me_3CCHCH_2$ or $Me(CH_2)_2CHCH_2$. In yet another embodiment, ligand L in formula (I) may be a silylalkyne having the formula $(R^9)_3SiCCR^{10}$ or $(R^{11})_3SiCCSi(R^{11})_3$ such as but not limited to $Me_3SiCCH$, $Me_2CH_2SiCCSiMe_3$, $(MeO)_2CH_2SiCCH$, or $(EtO)_2CH_2SiCCH$. In a still further embodiment, ligand L in formula (I) may be an allene such as but not limited to $CHCCCH_2$ or $MeCCCMe_2$. In another embodiment, ligand L in formula (I) may be an alkylisocyanide such as but not limited to MeCHNC. In the aforementioned formulas and throughout the specification, the term "Me" indicates a methyl group, "Et" indicates an ethyl group, "Pr" indicates a n-propyl group, and "i-Pr" indicates an isopropyl group.

In the above formula (I), the organometallic bond between the metal center and ligand (L) is either 2 single bonds or 1 single bond.

In one embodiment, a metal ketoiminate complex described herein where X is oxygen may be synthesized by reacting an amine functionalized with a group L with a β-diketone compound to form a β-ketoimine intermediate product. The amine may be, for example, a primary amine having the formula $H_2NR^4L$ wherein $R^4$ and L can be anyone of the groups or atoms described above. Non-limiting examples of a primary amine having the aforementioned formula include $H_2NCH_2CH_2OSiMe_2(C_2H_3)$. The β-diketone may be a compound having the formula $R^1C(O)CHR^2C(O)R^3$ wherein $R^1$, $R^2$, and $R^3$ can each independently be anyone of the groups or atoms described above. A non-limiting example of a β-diketone compound having the aforementioned formula is 2,4-pentanedione, 1,1,1-trifluoro-2,4-pentanedione, 2,4-hexanedione, and 3,5-heptanedione. One example would be reacting the amine $H_2NCH_2CH_2OSiMe_2(C_2H_3)$ and with 2,4-pentanedione to form the β-ketoimine intermediate $MeC(O)CH_2C(NCH_2CH_2OSiMe_2(C_2H_3))Me$. Once the β-ketoimine intermediate product is prepared, it is deprotonated (i.e., removing the acidic proton) and then complexed with a metal source in the presence of a base to provide the complex having the above formula (I).

In another embodiment, a metal diiminate complex described herein where X is $NR^5$ as described above may be synthesized by first preparing a β-ketoimine intermediate product as described above and then treating this with an alkylating agent such as triethyloxonium tetrafluoroborate or dimethyl sulfate and then reacting the resulting compound with an $R^5NH_2$ where $R^5$ is as described above to yield a β-diimine salt $[R^1C(R^5NH)CHR^2C(NR^4L)R^3]^+[V]^-$ as a second intermediate product where V is the conjugate base of the alkylating agent (for example, V is a tetrafluoroborate anion when triethyloxonium tetrafluoroborate is used). The group $R^5$ may or may not have a group L bonded to it. The resulting β-diimine salt ligand is twice deprotonated and then complexed with a metal source to provide the complex having the above formula (I).

The reaction of the amine with the β-diketone compound may be conducted in the presence of a solvent. Suitable solvents include, but are not limited to, ethers (e.g. diethylether ($Et_2O$), tetrahydrofuran ("THF"), di-n-butyl ether, 1,4-dioxane, or ethylene glycol dimethyl ether); nitriles (e.g. $CH_3CN$); or aromatic compounds (e.g. toluene), alone or in admixture thereof. In certain embodiments, the solvent is THF. The reaction temperature may range from −78° C. to the boiling point of the solvent. The reaction time may range from about 0 hours or instantaneous to about 48 hours, or from about 4 to about 12 hours. In certain embodiments, the intermediate product may be purified by standard procedures such as distillation, sublimation chromatography, recrystallization, and/or trituration. In some instances, however, the reaction of the amine with the β-diketone compound may be conducted in the absence of a solvent, particularly if the resulting β-ketoimine intermediate product is a liquid.

In certain embodiments, the β-ketoimine or β-diimine intermediate product to the final copper precursor may be one or more of the following there tautomeric isomers having the following formulas (II), (III), or (IV):

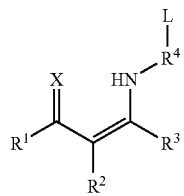
(II)

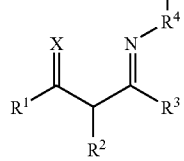
(III)

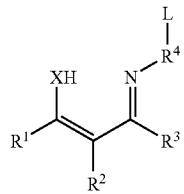
(IV)

In the above formulas, variables $R^1$, $R^2$, $R^3$, $R^4$, X and ligand (L) can each independently be any of the atoms or groups described herein.

An intermediate β-ketoimine product may need to be activated prior to its reaction with an amine or ammonia to give a β-diimine. For instance, the intermediate β-ketoimine product may first need to be alkylated by triethyloxonium tetrafluoroborate or by dimethylsulfate.

Equation (IV) shows an example of one embodiment of the preparation of a metal or a Cu(I) ketoiminate complex described herein. In this embodiment, the Cu(I) complex is prepared by deprotonating the β-ketoimine intermediate product from the reaction of the amine with the β-diketone compound, or deprotonating the β-diimine intermediate product from the reaction of a β-ketoimine intermediate product with an amine or ammonia, using one or more bases and then chelating to Cu(I) to give either the β-ketoimine or β-diimine complex, respectively. A non-limiting example of this reaction is illustrated in the following equation (4) showing the preparation of a β-ketoimine Cu(I) complex:

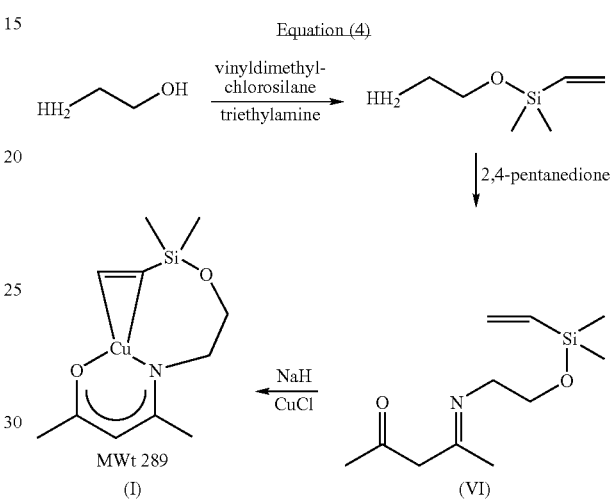

In Equation (4), the β-ketoimine intermediate product, which is a compound of formula (VI), is reacted with a base which is sodium hydride, a copper (I) source which is copper chloride to form the Cu(I) complex having the formula (I) and sodium chloride. Other bases that could be used in the above reaction include, but are not limited to, lithium hydride, n-butyl lithium, potassium hydride, sodium bis(trimethylsilylamide), lithium diisopropylamide, potassium t-butoxide, etc. Other sources of copper(I) that could be used in above reaction include, but are not limited to, copper(I) bromide, copper (I) iodide, copper(I) trifluoroacetate, copper(I) trifluoromethylsulfonate benxene adduct, copper(I)alkoxide, copper(I) amide, copper(I) acetate, copper(I) phenoxide, copper(I) acetamide, and copper(I) alkoxide. In embodiments where other metal or mixed copper precursors are prepared, the metal source is one or more metal salts containing the desired metal M. The anticipated yield of the metal or Cu(I) complex may range from about 5% to about 95% of the theoretical yield. In certain embodiments, the final product or the copper precursor, such as the Cu(I) complex, may be purified by standard procedures such as distillation, sublimation, chromatography, recrystallization, and/or trituration.

Alternatively, the copper precursors of this disclosure can be prepared by first synthesizing their analogous metal bis (ketoimine) and metal bis(diimine) compounds then reacting or reducing them with a metal source. Additional alternative pathways to synthesizing these precursors are possible, as illustrated by the non-limiting cases in the examples set out below.

In alternative embodiments, the β-ketoimine intermediate product can be reacted directly with a metal source, such as copper(I) aryl (e.g., copper mesitylene) or a copper alkoxide (e.g., $[CuOt-Bu]_4$) to form a metal or Cu(I) complex. In still further embodiments, the copper precursors can be prepared from its constituent parts, i.e., the β-ketoimine intermediate product and metal atom, in a suitable electrochemical process. These same synthetic pathways may be used to synthesize the metal diiminate complexes.

Yet another example of this approach is the reaction of ethanolamine ($H_2NCH_2CH_2OH$) with 2,4-pentanedione to give the first intermediate β-ketoimine product $MeC(O)CH_2C(NCH_2CH_2OH)Me$. The first intermediate β-ketoimine product $MeC(O)CH_2C(NCH_2CH_2OH)Me$ is reacted with chlorodimethylvinylsilane to give the second intermediate β-ketoimine product $MeC(O)CH_2C(NCH_2CH_2OSiMe_2(C_2H_3))Me$. The second intermediate β-ketoimine product is deprotonated and complexed to copper to give the provide the complex $Cu(MeC(O)CHC(NCH_2CH_2OSiMe_2(C_2H_3)Me)$.

As mentioned previously, the copper precursors described herein may be used as precursors for the deposition of a film comprising copper on a substrate. Examples of suitable substrates include but are not limited to, semiconductor materials such as gallium arsenide ("GaAs"), boronitride ("BN") silicon, and compositions containing silicon such as crystalline silicon, polysilicon, amorphous silicon, epitaxial silicon, silicon dioxide ("$SiO_2$"), silicon carbide ("SiC"), silicon oxycarbide ("SiOC"), silicon nitride ("SiN"), silicon carbonitride ("SiCN"), organosilicate glasses ("OSG"), organofluorosilicate glasses ("OFSG"), fluorosilicate glasses ("FSG"), and other appropriate substrates or mixtures thereof. Substrates may further comprise a variety of layers to which the film is applied thereto such as, for example, antireflective coatings, photoresists, organic polymers, porous organic and inorganic materials, metals such as copper and aluminum, or diffusion barrier layers (e.g., ruthenium, tantalum, titanium or combinations thereof). The copper precursors may be deposited using any of the techniques described herein or known in the art. Exemplary deposition techniques include, but are not limited to, chemical vapor deposition (CVD), cyclic chemical vapor deposition (CCVD), atomic layer deposition (ALD), plasma-assisted chemical vapor deposition (PACVD), and plasma-enhanced chemical vapor deposition (PECVD). In certain embodiments, the complexes can be used to grow thin films of metal or alloys thereof by CVD or ALD by reacting with a suitable reagent. In alternative embodiments, the copper precursors may react via a disproportionation reaction to provide a metal film or metal-containing film. In still further embodiments, the copper precursors can be reacted in the presence of a reducing agent to provide a metal film or metal-containing film. In one particular embodiment, the copper precursor $Cu(MeC(O)CHC(NCH_2CHMeOSiMe_2C_2H_3)Me)$ is used to deposit a copper film via a CVD process where it is reacted in the presence of a reducing agent comprising formic acid. While not wishing to be bound by theory, other ALD or CVD reducing reagents can also be used such as carboxylic acids, carboxylic esters in conjunction with water vapor, alcohols, hydrogen, silanes, boranes, alanes, ammonia or combinations thereof. In addition, plasma activation of the reducing agent can also be used in certain embodiments to achieve copper films at low temperatures.

For example, in one embodiment, reaction with a halogen source reagent may form a thin film of metal halide, whereas in another embodiment, reaction with a suitable oxidant such as water vapor may provide a metal oxide film. In yet another embodiment, reaction with an oxidant followed by a reducing agent such as hydrogen may form a metal film or metal/metal oxide mixed film. Alternatively, the copper precursor can be reacted with reagent gases activated by plasma either directly or downstream from a remote plasma source. The copper precursors disclosed herein can also be used mixed with other metal precursors in certain combinations to form metal films, metal-containing films, and/or metal alloy films. The films could be used as-deposited or, alternatively, could be reduced to the desired metal using a suitable reducing agent.

In certain embodiments, the copper precursors are deposited onto a substrate using a CVD or ALD technique. The deposition of the Cu(I) complexes may be conducted at temperatures of 400° C. or below, or 200° C. or below, or 100° C. or below. In a typical CVD deposition process, the copper precursor having the formula (I) is introduced into a reaction chamber such as a vacuum chamber. In certain embodiments, other chemical reagents, besides the copper precursor, may be introduced before, during, and/or after the introduction of the copper precursor. An energy source, such as, for example, thermal, plasma or other source, energizes the copper precursor and optional chemical reagents thereby forming a film on at least a portion of the substrate.

As mentioned previously, in certain embodiments, a chemical reagent may be introduced before, during, and/or after the introduction of the copper precursor into the reaction chamber. The choice of chemical reagent may depend upon the composition of the desired resultant films. For example, in one embodiment, reaction with a halogen-containing chemical reagent may form a film of metal halide, whereas in another embodiment, reaction with an oxidant chemical reagent will yield a metal oxide film. Exemplary chemical reagents include, but are not limited to oxidants such as $O_2$, NO, $NO_2$, $O_3$, CO, and $CO_2$; water; halides; halogen-containing silanes such as alkylchlorosilanes, alkylbromosilanes, or alkyliodosilanes; silicon halide compounds such as silicon tetrachloride, silicon tetrabromide, or silicon tetraiodide; halogenated tin compounds such as alkylchlorostannanes, alkylbromostannanes, or alkyliodostannanes; germane compounds such as alkylchlorogermanes, alkylbromogermanes, or alkyliodiogermanes; boron trihalide compounds such as borontrichloride, boron tribromide, or boron triodide; aluminum halide compounds such as aluminum chloride, aluminum bromide, or aluminum iodide; alkylaluminum halides; gallium halide compounds such as gallium trichloride, gallium tribromide, or gallium triodide; or combinations thereof. It is also envisioned that derivatives of the above compounds may also be used. The chemical reagents may be delivered directly as a gas to the reaction chamber, delivered as a vaporized liquid, a sublimed solid and/or transported by an inert carrier gas into the reaction chamber. Examples of inert carrier gases include nitrogen, hydrogen, argon, xenon, etc.

In certain embodiments, the metal film may form on the substrate surface by a disproportionation reaction such as that depicted for the Cu(I) complex shown in Equation 5 below.

Equation 5

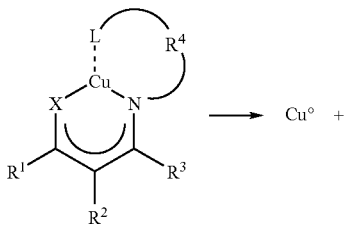

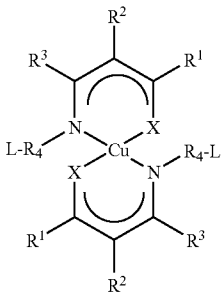

In another embodiment, a metal film may be deposited onto the surface of a substrate in the presence of a reducing agent to, for example, reduce the film to metal. The copper precursor having the formula (I) may be introduced into a CVD or ALD reactor along with one or more reducing agents. Examples of suitable reducing agents include, but are not limited to, hydrogen gas, carboxylic acids (e.g., formic acid, acetic acid, propionic acid, lauric acid, stearic acid, oxalic acid, citric acid, benzoic acid, glutonic acid, etc.), alcohols, hydrogen plasma, carboxylic esters, remote hydrogen plasma, silanes (e.g., diethylsilane, ethylsilane, dimethylsilane, phenylsilane, silane, disilane, aminosilanes), boranes (e.g., borane, diborane), alanes, germanes, hydrazines, ammonia, or mixtures thereof. In one particular embodiment, formic acid is used as a reducing agent. In certain embodiments, the reducing agent may be introduced in gaseous form. In this or other embodiments, the copper precursor having formula (I) is dissolved in a suitable organic solvent to provide a solution and the resulting solution is vaporized in a liquid evaporator to provide a vapor which is fed into a CVD or ALD reactor where it is reduced by contacting it with a one or more reducing agents.

In one particular embodiment, formic acid is used as a reducing agent to provide relatively smooth copper films at relatively low deposition temperatures and useful deposition rates. In this embodiment, the surface roughness of the film or Ra measured in Å decreased substantially when compared to equivalent copper films that were not deposited using a carboxylic acid comprising formic acid. In particular, the surface roughness of the resultant copper film was 200 Å or less, or 100 Å or less, or 50 Å or less, or 20 Å or less. In this or other embodiments, the smoothness of a copper film grown by ALD or CVD using one or more copper precursor, such as, for example, Cu(MeC(O)CHC(NCH$_2$CHMeOSiMe$_2$ C$_2$H$_3$)Me), may be controlled by the relative ratio of copper precursor to carboxylic acid, such as, for example, formic acid, where a higher acid:precursor ratio results in a smoother copper film.

In certain embodiments, water vapor may also be used by itself or in addition to the reducing agents described herein to help catalyze the deposition of a copper film.

In certain embodiments, a metal film is deposited from the Cu(I) complex of the formula (I) via an ALD deposition process. During a typical ALD process, one or more gaseous or vaporized precursors are introduced into the process chamber which houses the substrate in alternating pulses within a process cycle. Preferably, each process cycle forms no more than about one monolayer of material by adsorption and preferably by chemisorption. The number of process cycles used to grow the layer depends on the thickness desired but may generally exceed 1,000 cycles. For semiconductor devices, the process cycle is repeated until the barrier or seed layer within the dual damascene structure has a thickness sufficient to perform its desired function.

During ALD processing, the substrate is kept at a temperature range that facilitates chemisorption, i.e., is low enough to maintain intact bonds between adsorbed species and the underlying substrate yet high enough to avoid condensation of the precursors and to provide sufficient activation energy for the desired surface reactions in each process cycle. The process chamber temperature may range from 0° C. to 400° C., or from 0° C. to 300° C., or from 0° C. to 275° C. The pressure within the process chamber during ALD processing may range from 0.1 to 1000 Torr, of from 0.1 to 15 Torr, or from 0.1 to 10 Torr. It is understood, however, that the temperature and pressure for any particular ALD process may vary depending upon the one or more precursors involved.

Any of the aforementioned film formation methods described herein, as well as other film formation methods known in the art, may be used alone or in combination. For example, in one embodiment, a mixed composition copper-containing film may be formed by sequentially depositing a copper oxide film followed by a copper metal film and then reducing the multilayers to provide a pure copper film.

In certain embodiments, the copper precursor described herein may be dissolved in a suitable solvent such as an amine (e.g., triethylamine), an ether (e.g., THF), an aromatic (e.g., toluene) or any other solvent disclosed herein, to form a solution. The resulting solution may be flash vaporized in a Direct Liquid Injection (DLI) system for vapor delivery into an ALD or CVD reaction chamber. In other embodiments, the complexes described herein can be dissolved in a stabilizing liquid such as olefins or alkynes prior to introduction to a DLI system.

EXAMPLES

In the following examples, the G.C.M.S. Spectra for the examples were performed on a Hewlett Packard 5890 Series 11 G.C. and 5972 series mass selective detector with a HP-5MS. The NMR analyses for the examples were obtained on a Bruker AMX 500 spectrometer operating at 500 MHz. Chemical shifts were set from C$_6$D$_6$ at 7.16 ppm in $^1$H and 128.39 parts per million (ppm) in $^{13}$C. X-ray analysis was conducted on a Bruker D8 platform diffractometer equipped with an APEX CCD detector and a Kryoflex cryostat.

Example 1

Synthesis of Cu(MeC(O)CHC(NCH$_2$CHMeOSiMe$_2$ C$_2$H$_3$)Me) precursor

Step 1: Forming MeC(O)CHC(HNCH$_2$CHMeOH)Me or Ketoimine Intermediate 150 g (2.0 moles 1-amino-2-propanol) was added to 200 g (2.0 moles) of 2,4-pentanedione stirred in 1.0 liter of hexane solvent containing 200 g of sodium sulfate drying agent for 1 hour. The hexane was then decanted off and 500 ml of tetrahydrofuran (THF) solvent added to dissolve all of the crude product. This solution was then decanted into a fresh flask containing 200 g of fresh sodium sulfate and stirred for 1 hour. The THF solution was then decanted off and stored in a freezer overnight to crystallize. The supernatant liquid was decanted off and the remaining solid pumped dry. The crude solid was then melted under vacuum to 130 C and volatiles pumped away to a liquid nitrogen cooled vacuum trap. Yield=197.5 g (63%), The GCMS results for the product showed it to be >99% pure and its mass spectra identified as that of the desired product showing a parent ion fragment at 157 mu.

Step 2: Forming MeC(O)CHC (HNCH$_2$CHMeOSiMe$_2$C$_2$H$_3$)Me or Silylated Ketoimine Intermediate A solution of 163.4 g (1.04 moles) of MeC(O)CHC (NHCH$_2$CHMeOH)Me dissolved in 1.5 liters of THF was added to a suspension of 27.5 g (1.14 moles) sodium hydride in 30 ml of THF under a blanket of nitrogen. When evolution of hydrogen stopped, the mixture was then stirred for an additional 1 hour. 151 g (1.25 moles, i.e., 20% excess) chlorodimethylvinylsilane was then added over 1 hour and the mixture stirred for 1 hour. The mixture was then filtered and the THF and excess reagents stripped off to yield a crude product. This was then vacuum distilled at 100° C. to yield the finished product. Yield=209 g (83%). It was identified by GCMS which showed parent ion fragment at 241 mu. The NMR results for the product were as follows: $^1$H NMR: (500 MHz, C$_6$D$_6$): δ=0.21 (s, 3H), δ=1.9 (s, 3H), δ=0.88 (d, 3H), δ=1.49 (s, 3H), δ=2.05 (s, 3H), δ=2.6 (m, 1H), δ=2.76 (m, 1H), δ=3.54 (m, 1H), δ=4.9 (bs, 1H), δ=5.74 (dd, 1H), δ=5.9 (dd, 1H), δ=6.2 (dd, 1H), δ=11.27 (bs, 1H); $^{13}$C NMR: (500 MHz, C$_6$D$_6$): δ=−1.42 (s, 1C), δ=−1.15 (s, 1C), δ=19.1 (s, 1C), δ=21.7 (s, 1C), δ=29.3 (s, 1C), δ=50.8 (s, 1C), δ=68.9 (s, 1C), δ=68.9 (s, 1C), δ=96.0 (s, 1C), δ=133.6 (s, 1C), δ=138.5 (s, 1C), δ=162.3 (s, 1C), δ=194.7 (s, 1C).

Step 3: Synthesis of Cu(MeC(O)CHC(NCH$_2$CHMeOSiMe$_2$ C$_2$H$_3$)Me) copper precursor Under a blanket of nitrogen, 45 g (0.45 moles, i.e., 10% excess) copper chloride was added to 81 g (0.8 moles) of trimethylvinylsilane in 50 ml of THF and stirred for 30 minutes to yield a clear solution. To this was added a solution of 44 g (0.45 moles) of sodium t-butoxide dissolved in 100 ml of THF and the resulting mixture was stirred for 30 minutes. To this mixture was added 102 g (0.4 moles) of product of step 2 was added drop wise over 30 minutes and the resulting mixture stirred overnight. The solvent was then stripped off under vacuum and the resulting crude material was heated under vacuum to 140 C to drive off the volatile copper complex as a liquid which solidified upon cooling. This solid was then purified by vacuum sublimation to yield the final product as colorless prisms. Yield=105 g (85%). The NMR results for the product were as follows: $^1$H NMR: (500 MHz, C$_6$D$_6$): δ=0.10 (m, 6H), δ=1.03 (m, 3H), δ=0.1.57 (d, 3H), δ=2.1 (s, 3H), δ=3.4-4.2 (m, 5H), δ=5.0 (d, 1H). The GCMS results for the product confirmed its identity by showing a strong parent ion fragment at 303 mu.

Example 2

Figure 6:
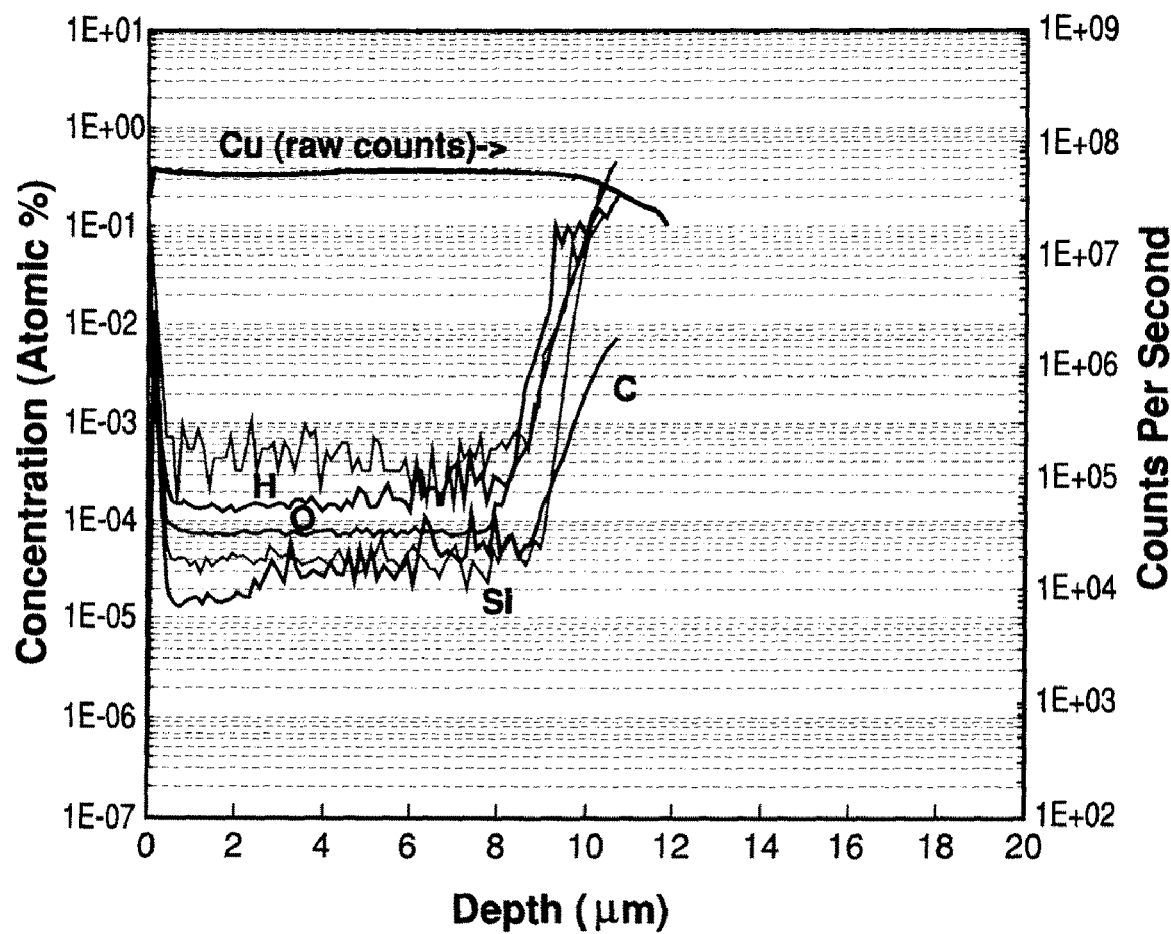
FIG. 6 provides the secondary ion mass spectrometry (SIMS) profile of a copper film deposited by CVD onto titanium nitride using the copper(N(2(vinyldimethylsiloxy)propyl)-2-imino-4-pentenoate) precursor according to Example 2.
Figure 7:
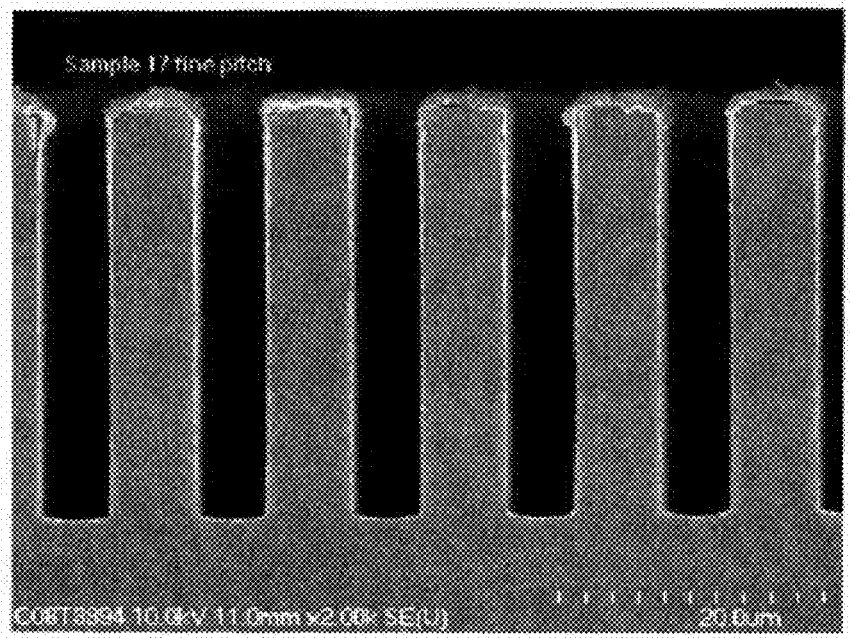
FIGS. 7, 8, 9, and 10 provides scanning electron micrograph (SEM) of a copper film deposited by CVD onto a patterned TaN substrate using the copper(N(2(vinyldimethylsiloxy)propyl)-2-imino-4-pentenoate) precursor according to Example 3 which shows the trench, top, bottom and sidewall of the film, respectively.
Figure 8:
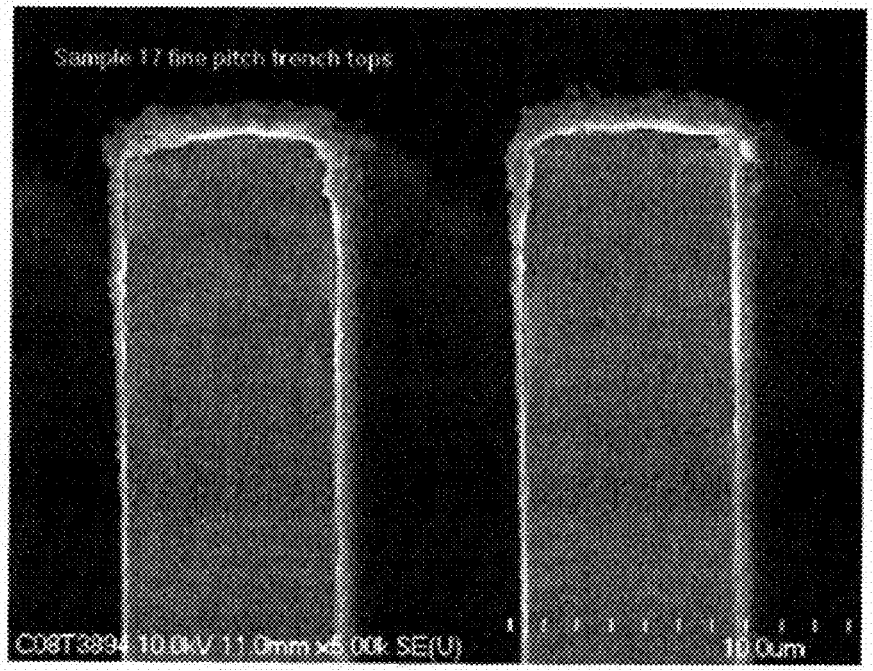
Figure 9:
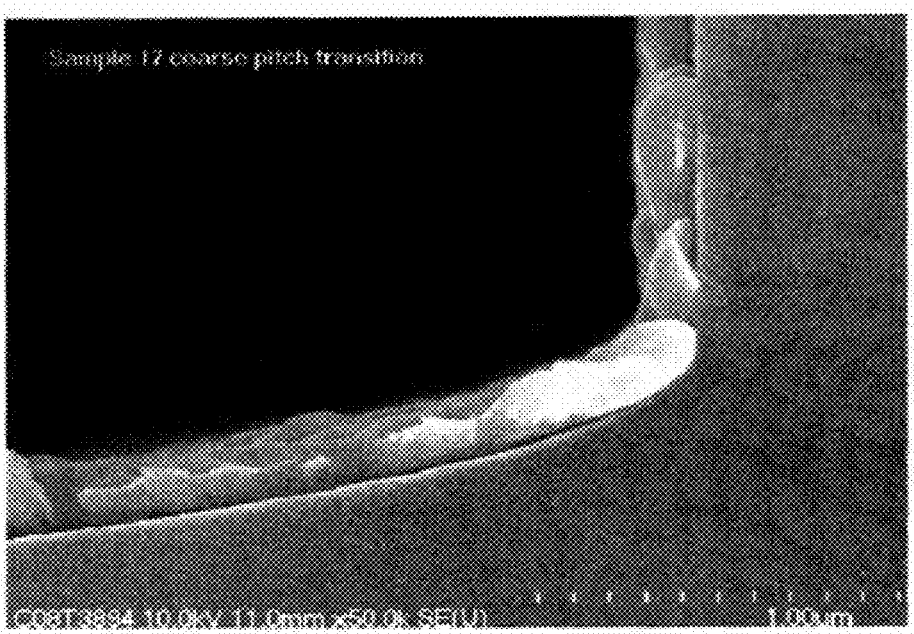
Figure 10:
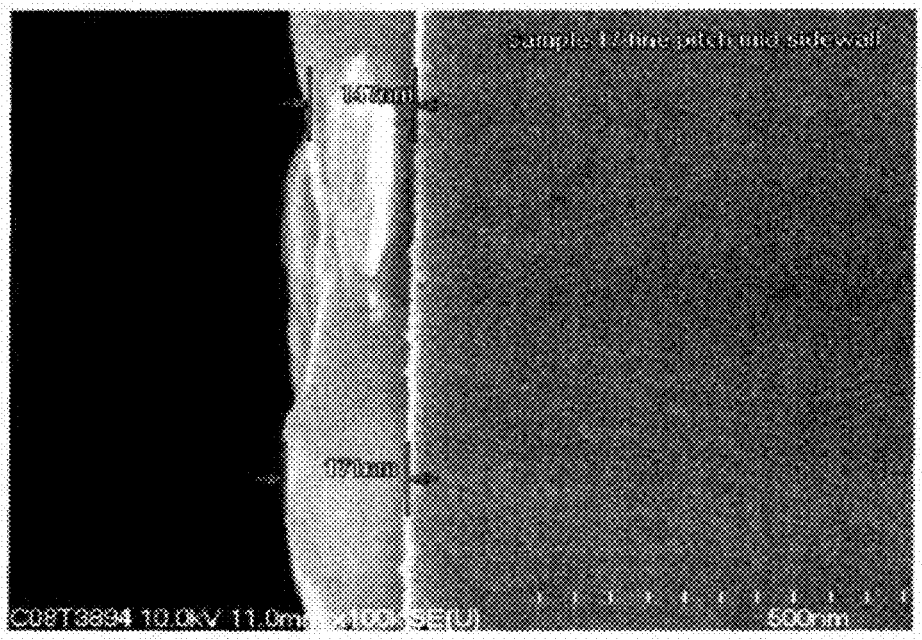

CVD Deposition of a Copper Film Using the Cu(MeC(O)CHC(NCH$_2$CHMeOSiMe$_2$ C$_2$H$_3$)Me) Precursor A copper film was deposited onto a titanium nitride (TiN) substrate using the Cu(MeC(O)CHC(NCH$_2$CHMeOSiMe$_2$ C$_2$H$_3$)Me) precursor in a hot wall CVD laboratory scale reactor using the conditions described in the following Table I and using formic acid as a reducing agent. A pure copper film of approximately 5 microns thick was grown, as determined by Secondary Ion Mass Spectrometry (SIMS) analysis, as shown in FIG. 6, which showed no detectable amounts of carbon, hydrogen, nitrogen, oxygen or silicon meaning that the copper film is >99.99 atomic % pure copper. Note that the depth profile was stopped before the bottom of the copper film was reached.

TABLE I

| CVD copper process conditions | |
|---|---|
| TiN wafer temperature ° C. | 250 |
| Copper Precursor source temperature (° C.) | 120 |
| CVD chamber pressure (Torr) | 2 |
| Copper precursor helium carrier gas flow (sccm) | 25 |
| Formic acid reagent flow (sccm) | 150 |
| Run time (minutes) | 30 |

Example 3

CVD Deposition of a Copper Film Using the Cu(MeC(O)CHC(NCH$_2$CHMeOSiMe$_2$ C$_2$H$_3$)Me) Precursor A copper film was deposited onto a patterned tantalum nitride (TaN) substrate using the Cu(MeC(O)CHC (NCH$_2$CHMeOSiMe$_2$ C$_2$H$_3$)Me) precursor in a hot wall CVD laboratory scale reactor using the conditions described in the following Table II and using formic acid as a reducing agent. The copper film was deposited as a conformal layer into a large scale trench feature and had dimensions typically found in TSV/3-D packaging, as evidenced by FIGS. 7, 8, 9 and 10 which provide four Scanning Electron Microscope (SEM) images of the trench, top, bottom, and sidewall views, respectively, of the copper film.

TABLE II

| CVD copper process conditions | |
|---|---|
| TaN wafer temperature (° C.) | 225 |
| Copper Precursor source temperature (° C.) | 120 |
| CVD chamber pressure (Torr) | 5 |
| Copper precursor helium carrier gas flow (sccm) | 100 |
| Formic acid reagent flow (sccm) | 150 |
| Run time (minutes) | 60 |

Example 4

Figure 11:
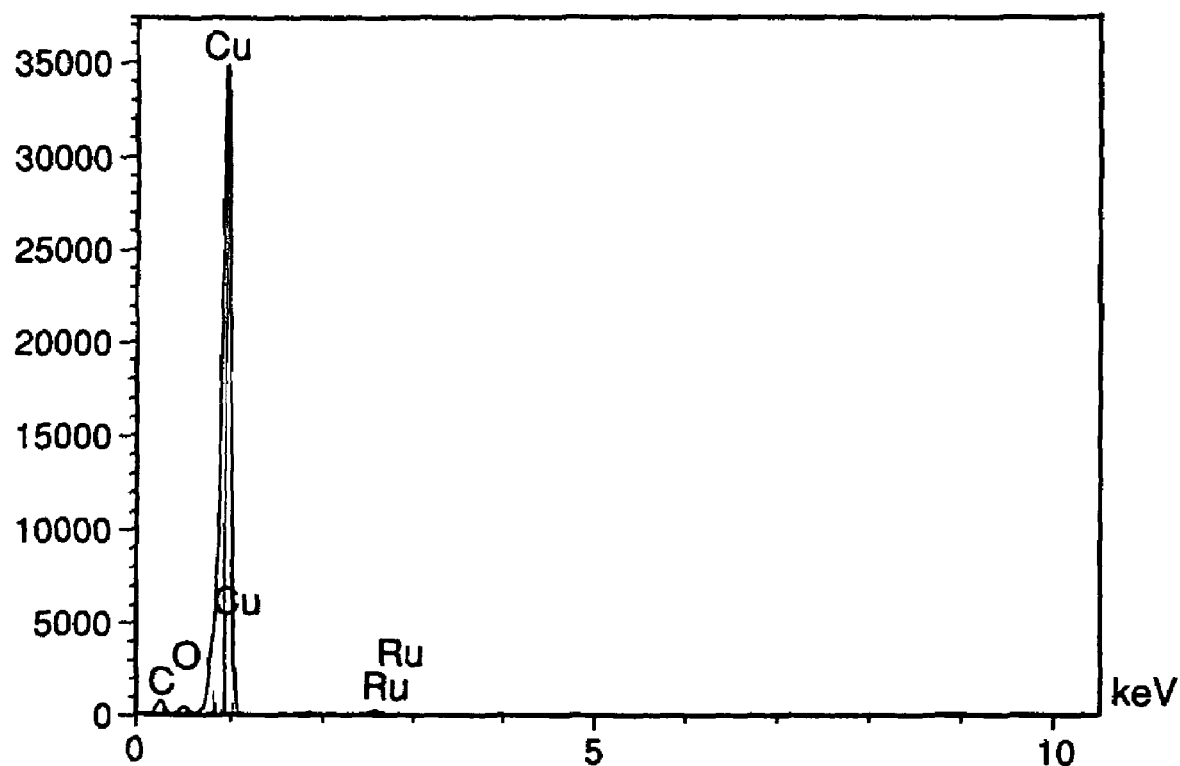
FIG. 11 provides the Energy Dispersive X-ray (EDX) of a copper film deposited onto a ruthenium barrier layer by CVD according to Example 4.

CVD Deposition of a Copper Film Using the Cu(MeC(O)CHC(NCH$_2$CHMeOSiMe$_2$ C$_2$H$_3$)Me) Precursor A copper film was deposited onto a ruthenium substrate using the Cu(MeC(O)CHC(NCH$_2$CHMeOSiMe$_2$ C$_2$H$_3$)Me) precursor in a hot wall CVD laboratory scale reactor using the conditions described in the following Table III and using formic acid as a reducing agent. A pure copper film of approximately 1000 Angstrom thick (as measured using a Decktak stylus profilometer) was grown, as determined by EDX and shown in FIG. 11.

TABLE III

| CVD copper process conditions | |
| --- | --- |
| Ruthenium wafer temperature (° C.) | 125-130 |
| Copper Precursor source temperature (° C.) | 85 |
| CVD chamber pressure (Torr) | 2 |
| Copper precursor helium carrier gas flow (sccm) | 25 |
| Formic acid reagent flow (sccm) | 150 |
| Formic acid temperature ° C. | 20 |
| Run time (minutes) | 30 |

Example 5

Enhanced Copper Film Smoothness by Additional Formic Acid

The experiment of example 5 was repeated, but this time the source temperature of the formic acid was increased to 25° C. and using the additional deposition conditions provided in Table IV. This resulted in a smoother copper film, as measured by a decrease in surface roughness, Ra expressed in Angstroms (Å) using a Dektak stylus profilometer manufactured by Veeco.

TABLE IV

| Decreased CVD copper film roughness on ruthenium at 125-130° C. by additional formic acid | | |
| --- | --- | --- |
| Formic acid temperature (° C.) | Formic acid flow (sccm) | Copper film roughness: Ra (Å) |
| 20 | 150 | 187 |
| 25 | 200 | 11 |

Example 6

Thermal Stability of Copper(N(2(vinyldimethylsiloxy)propyl)-2-imino-4-pentenoate) compared to Copper(N(2(vinyldimethylsiloxy)ethyl)-2-imino-4-pentenoate)

The thermal stability of the copper(N(2(vinyldimethylsiloxy)propyl)-2-imino-4-pentenoate) or Cu(MeC(O)CHC(NCH$_2$CHMeOSiMe$_2$ C$_2$H$_3$)Me)) precursor was compared to that of the copper(N(2(vinyldimethylsiloxy)ethyl)-2-imino-4-pentenoate). The TGA in FIG. 1 shows that copper (N(2(vinyldimethylsiloxy)propyl)-2-imino-4-pentenoate) essentially undergoes complete evaporation (dotted line) in the TGA experiment with an involatile residue of 1.22%, which is within the experimental error of the technique. In addition, FIG. 1 also provides the DSC (solid line) which shows only a smooth endotherm of evaporation with no exothermic excursions which would indicate thermal decomposition to be occurring. This indicates that no extraneous gas phase species due to thermal decomposition are emitting from the precursor which could pollute the vapor stream feed to an ALD or CVD reactor. The weight loss is observed to abruptly stop at 250° C., which is consistent with the fact there is substantially no species of lower volatility left as a residue in the pan as a consequence of thermal degradation of the precursor which could then subsequently continue to lose weight as the temperature increases further. Further, the weight loss also points to no accumulation of involatile residue in the precursor container.

Figure 2:
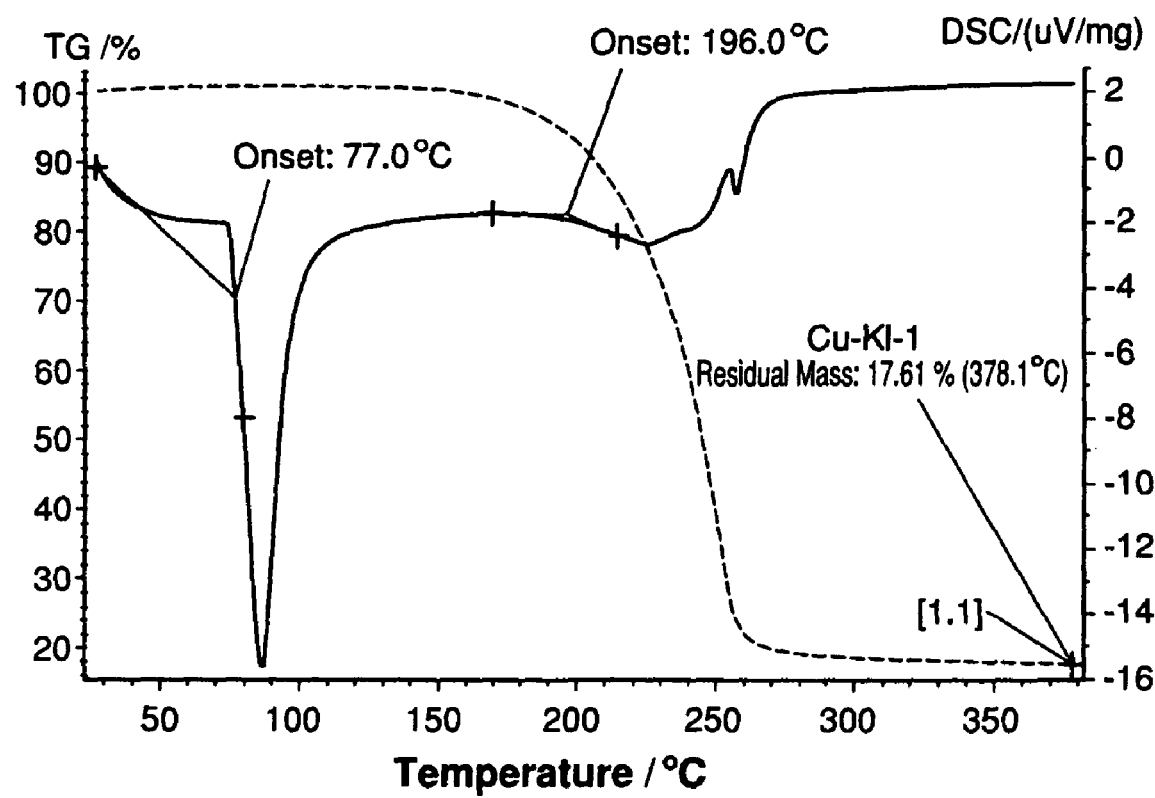
FIG. 2 provides the TGA of the evaporation of the precursor copper(N(2(vinyldimethylsiloxy)ethyl)-2-imino-4-pentenoate) or Cu(MeC(O)CHC(NCH$_2$CH$_2$OSiMe$_2$C$_2$H$_3$)Me).

FIG. 2 provides the TGA for copper(N(2(vinyidimethylsiloxy)ethyl)-2-imino-4-pentenoate) which differs from that in FIG. 1 in that it clearly shows a substantial final involatile residue of 17.6 wt % and an abrupt change in weight loss at 260° C. followed by a slower weight loss from a new less volatile residual species formed by the thermal decomposition of the sample, ultimately yielding a final 15.8% residue. Additionally, the DSC in FIG. 2 shows a slight initial endotherm of evaporation followed by an exotherm of decomposition at 230° C. Thus, by comparing FIG. 1 and FIG. 2, it is evident that copper(N(2(vinyldimethylsiloxy)propyl)-2-imino-4-pentenoate) is a thermally stable molecule which can cleanly evaporate without decomposition when compared to copper(N(2(vinyldimethylsiloxy)ethyl)-2-imino-4-pentenoate) which shows thermal degradation under the same conditions. It is to be noted that the copper(N(2(vinyldimethylsiloxy)ethyl)-2-imino-4-pentenoate) precursor is thermally stable below 230° C. thereby indicating that it can be used as a precursor below this temperature. However, the superior and unexpected additional thermal stability of copper(N(2(vinyldimethylsiloxy)propyl)-2-imino-4-pentenoate) may render it more a desirable precursor under certain deposition conditions.

Figure 3:
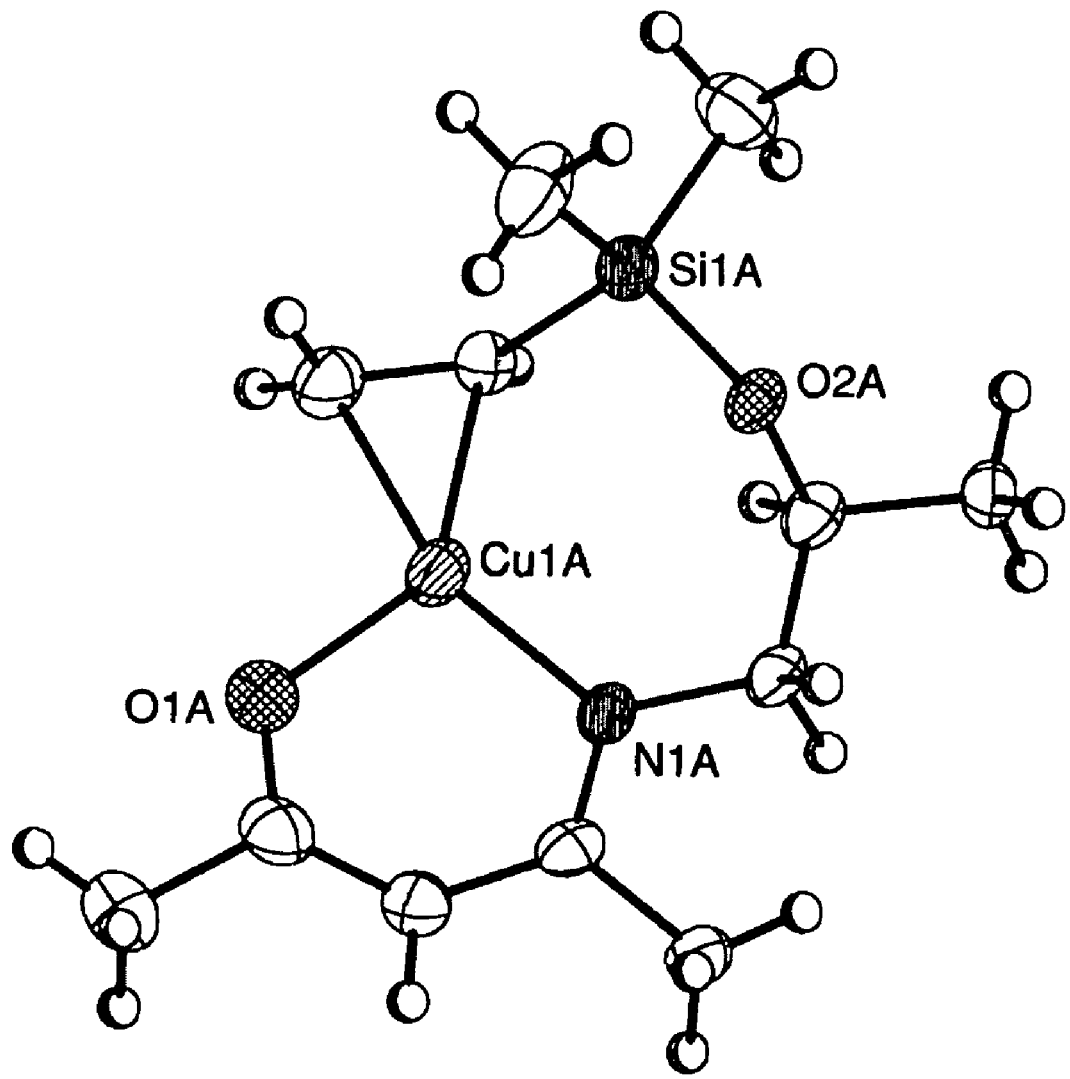
FIG. 3 provides an exemplary structure of one of the copper precursors described herein or copper(N(2(vinyldimethylsiloxy)propyl)-2-imino-4-pentenoate).
Figure 4:
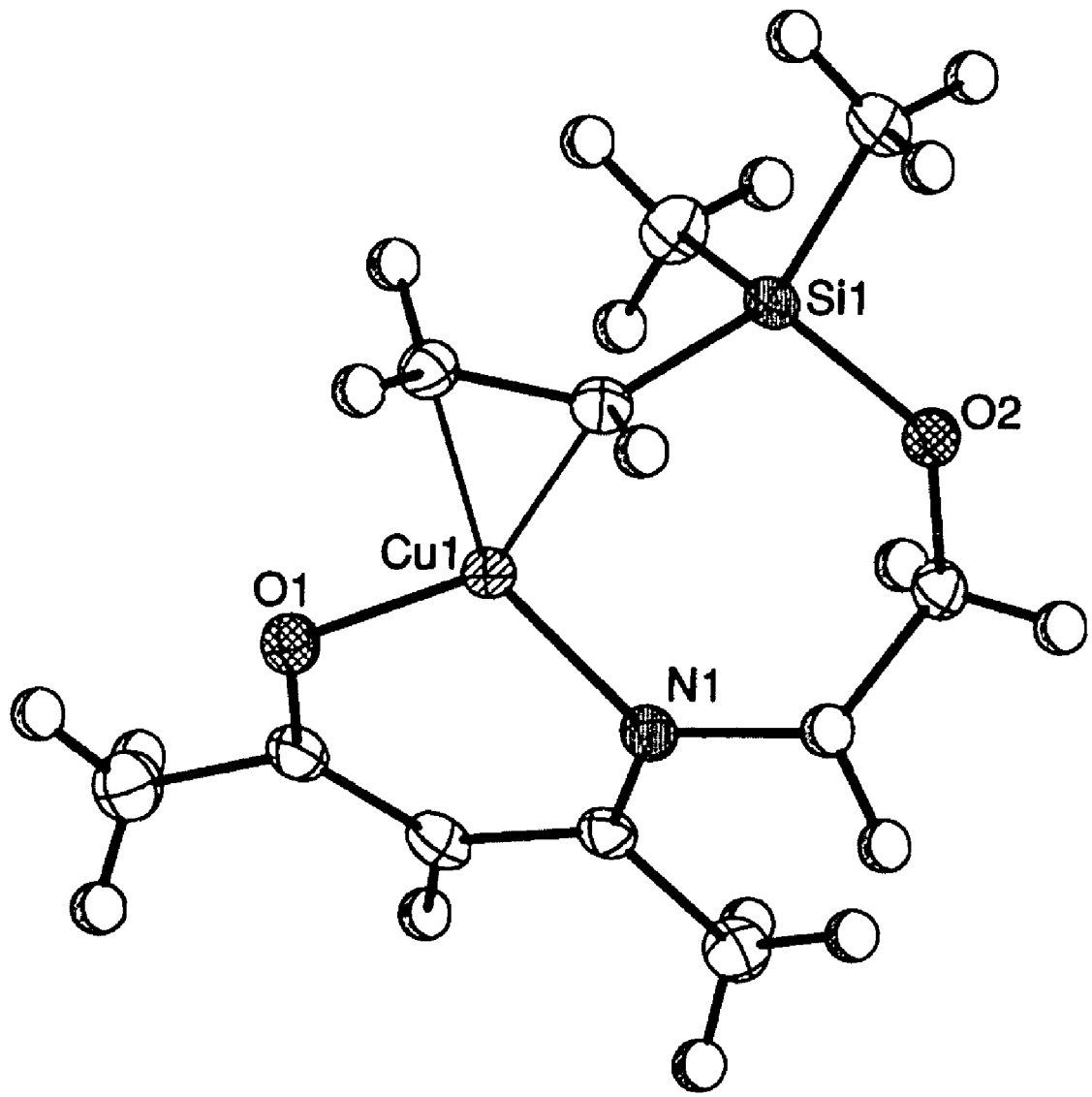
FIG. 4 provides an exemplary structure of one of the copper precursors described herein or copper(N(2(vinyldimethylsiloxy)ethyl)-2-imino-4-pentenoate).
Figure 5:
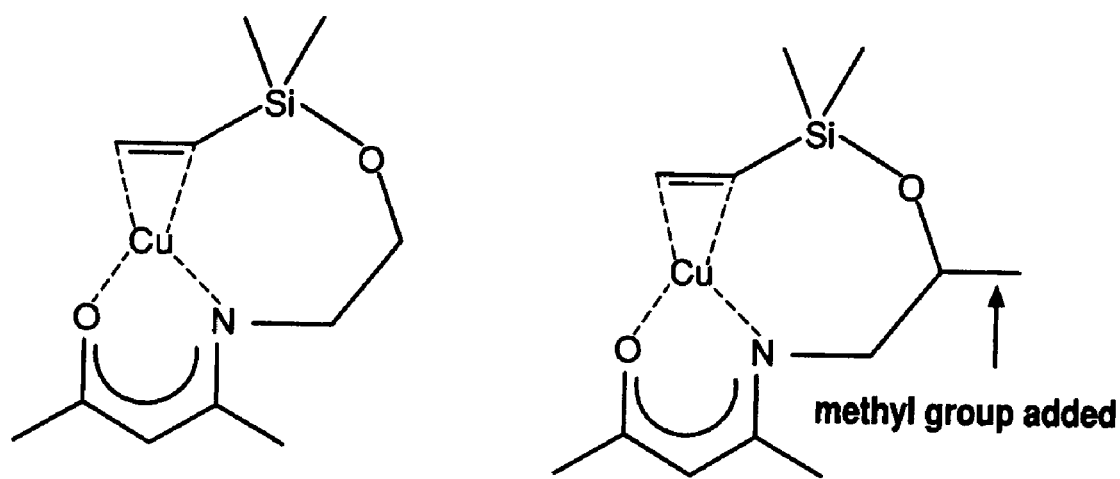
FIG. 5 provides a comparative of the structure of the copper (N(2(vinyldimethylsiloxy)propyl)-2-imino-4-pentenoate) precursor and copper(N(2(vinyldimethylsiloxy)ethyl)-2-imino-4-pentenoate) precursor highlighting where the methyl group is added onto the copper(N(2(vinyldimethylsiloxy)propyl)-2-imino-4-pentenoate) precursor.

The only structural difference between copper(N(2(vinyidimethylsiloxy)ethyl)-2-imino-4-pentenoate) and copper(N(2(vinyldimethylsiloxy)propyl)-2-imino-4-pentenoate) is that the latter copper precursor bears a methyl group in place of a hydrogen atom in copper(N(2(vinyidimethylsiloxy)ethyl)-2-imino-4-pentenoate). The position of the hydrogen in copper(N(2(vinyldimethylsiloxy)ethyl)-2-imino-4-pentenoate) that is replaced by a methyl group provides the precursor copper(N(2(vinyldimethylsiloxy)propyl)-2-imino-4-pentenoate) where the carbon atom is connected to the oxygen which is connected to the silicon atom. FIGS. 3 and 4 provide the structures of the copper(N(2(vinyldimethylsiloxy)propyl)-2-imino-4-pentenoate) (or Cu(MeC(O)CHC(NCH$_2$CHMeOSiMe$_2$ C$_2$H$_3$)Me)) and copper(N(2(vinyldimethylsiloxy)ethyl)-2-imino-4-pentenoate) (or Cu(MeC(O)CHC(NCH$_2$CH$_2$OSiMe$_2$C$_2$H$_3$)Me)) precursors, respectively. FIG. 5 shows the structures of these precursors indicating where the methyl group is attached in the latter molecule by substituting it for a hydrogen atom in the same position. It is believed that the simple substitution of a methyl group for a hydrogen atom leads to a remarkable and totally unexpected increase in thermal stability between the two precursors under certain deposition conditions.

We claim:

1. A copper precursor for depositing films via chemical vapor deposition or atomic layer deposition represented by formula (I):

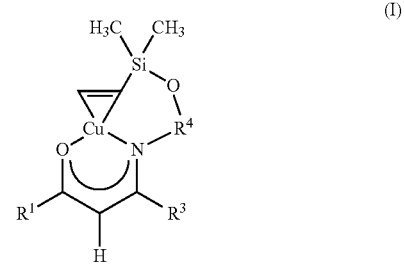

wherein $R^1$ and $R^3$ are each independently selected from an alkyl having a formula $C_nH_{2n+1}$ wherein n is a number ranging from 1 to 4; wherein $R^4$ is selected from the group consisting of propyl, butyl and pentyl, with the proviso that $R^4$ is always bonded to the oxygen through the second carbon of $R^4$ from the nitrogen atom.

2. $Cu(MeC(O)CHC(NCH_2CHMeOSiMe_2C_2H_3)Me)$.

3. $Cu(MeC(O)CHC(NCH_2CHEtOSiMe_2C_2H_3)Me)$.

4. $Cu(MeC(O)CHC(NCH_2CHPrOSiMe_2C_2H_3)Me)$.

5. An electronic device comprising a copper film wherein the film is deposited via a process selected from atomic layer deposition or chemical vapor deposition from a reaction mixture comprising $Cu(MeC(O)CHC(NCH_2 CHMeO SiMe_2 C_2H_3)Me)$ and a reducing agent comprising at least one selected from hydrogen, a carboxylic acid, an alcohol, a carboxylic ester, a silane, a borane, an alane, a germane, a hydrazine, ammonia, or mixtures thereof.

6. The electronic device of claim 5 wherein the reducing agent comprises carboxylic acid.

7. The electronic device of claim 6 wherein the carboxylic acid comprises formic acid.

8. A process for forming a copper film on an at least one surface of a diffusion barrier layer, the process:

providing the at least one surface of the diffusion barrier layer; and forming the copper film on at least a portion of the surface by either a chemical vapor deposition process or an atomic layer deposition process with a copper precursor having the following formula (I):

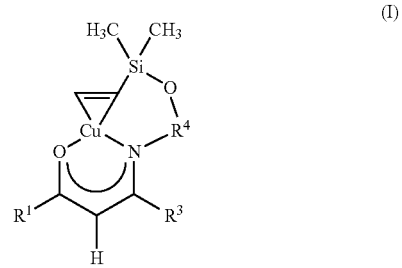

wherein $R^1$ and $R^3$ are each independently selected from an alkyl having a formula $C_nH_{2n+1}$ wherein n is a number ranging from 1 to 4; wherein $R^4$ is selected from the group consisting of propyl, butyl and pentyl, with the proviso that $R^4$ is always bonded to the oxygen through the second carbon of $R^4$ from the nitrogen atom.

9. The process of claim 8 wherein the forming process further comprises introducing a reducing agent comprising a carboxylic acid.

10. The process of claim 9 wherein the carboxylic acid comprises formic acid.

11. The process of claim 10 wherein the copper film comprises a surface roughness (Ra) of 20 (Å) or less.

12. The process of claim 8 wherein the diffusion barrier layer comprises ruthenium.

13. The process of claim 8 wherein the diffusion barrier layer comprises titanium.

14. The process of claim 8 wherein the diffusion barrier layer comprises tantalum.

* * * * *